United States Patent
Josse

(10) Patent No.: US 11,224,415 B1
(45) Date of Patent: Jan. 18, 2022

(54) TISSUE RETRACTOR

(71) Applicant: Warsaw Orthopedic, Inc., Warsaw, IN (US)

(72) Inventor: Loic Josse, Collierville, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

(21) Appl. No.: 16/926,173

(22) Filed: Jul. 10, 2020

(51) Int. Cl.
A61B 17/02 (2006.01)
A61M 29/02 (2006.01)
A61B 17/00 (2006.01)

(52) U.S. Cl.
CPC ...... A61B 17/0206 (2013.01); A61B 17/0218 (2013.01); A61M 29/02 (2013.01); A61B 2017/00367 (2013.01); A61B 2017/00477 (2013.01)

(58) Field of Classification Search
CPC . A61B 17/02; A61B 17/0206; A61B 17/0218; A61B 17/025; A61B 17/0281; A61B 17/0293; A61B 2017/00367
USPC .................................................. 600/201–246
See application file for complete search history.

(56) References Cited

U.S. PATENT DOCUMENTS

| 4,034,746 | A | 7/1977 | Williams |
| 5,681,265 | A | 10/1997 | Maeda et al. |
| 5,931,777 | A | 8/1999 | Sava |
| 5,993,385 | A | 11/1999 | Johnston et al. |
| 6,074,343 | A | 6/2000 | Nathanson et al. |
| 6,193,651 | B1 | 2/2001 | DeFonzo |
| 6,712,795 | B1 | 3/2004 | Cohen |
| 6,945,933 | B2 | 9/2005 | Branch et al. |
| 7,141,015 | B2 | 11/2006 | Ruane |
| 7,407,483 | B2 | 8/2008 | Perez-Cruet et al. |
| 7,481,766 | B2 | 1/2009 | Lee et al. |
| 7,491,168 | B2 | 2/2009 | Raymond et al. |
| 7,537,565 | B2 | 5/2009 | Bass |
| 7,780,594 | B2 | 8/2010 | Hutton |
| 7,819,801 | B2 | 10/2010 | Miles et al. |

(Continued)

FOREIGN PATENT DOCUMENTS

| EP | 3270792 B1 | 5/2020 |
| WO | 2012040206 A1 | 3/2012 |

OTHER PUBLICATIONS

Written Opinion, PCT/US2021/040225 dated Nov. 11, 2021, (10 PP).

Primary Examiner — Eduardo C Robert
Assistant Examiner — Christina Negrellirodriguez
(74) Attorney, Agent, or Firm — Fox Rothschild LLP

(57) ABSTRACT

A retractor system for enabling access to a surgical site is disclosed. The retractor system may include a primary retractor assembly configured to open and close a first arm and a second arm along a first path of travel. The primary retractor assembly may include a handle assembly having first and second handles configured to open and close the first and second arms, and the first and second arms may be operably coupled to first and second blades, respectively. The retractor system may further include a secondary retractor assembly configured to couple and uncouple with the primary retractor assembly and independently extend and contract a third arm and optionally a fourth arm. The third arm and optional fourth arm may be operably coupled to third and fourth blades, respectively. The inclination of each blade may be independently adjusted and each arm may also be independently moved.

20 Claims, 19 Drawing Sheets

(56) References Cited

U.S. PATENT DOCUMENTS

| | | | |
|---|---|---|---|
| 7,850,608 | B2 | 12/2010 | Hamada |
| 7,892,173 | B2 | 2/2011 | Miles et al. |
| 7,981,031 | B2 | 7/2011 | Frasier et al. |
| 8,062,217 | B2 | 11/2011 | Boucher et al. |
| 8,262,570 | B2 | 9/2012 | White et al. |
| 8,303,498 | B2 | 11/2012 | Miles et al. |
| 8,323,185 | B2 | 12/2012 | Perez-Cruet et al. |
| 8,343,048 | B2 | 1/2013 | Warren, Jr. |
| 8,353,826 | B2 | 1/2013 | Weiman |
| 8,355,780 | B2 | 1/2013 | Miles et al. |
| 8,388,527 | B2 | 3/2013 | Miles et al. |
| 8,480,576 | B2 | 7/2013 | Sandhu |
| 8,500,634 | B2 | 8/2013 | Miles et al. |
| 8,517,935 | B2 | 8/2013 | Marchek et al. |
| 8,550,994 | B2 | 10/2013 | Miles et al. |
| 8,556,808 | B2 | 10/2013 | Miles et al. |
| 8,579,809 | B2 | 11/2013 | Parker |
| 8,602,984 | B2 | 12/2013 | Raymond et al. |
| 8,668,715 | B2 | 3/2014 | Sandhu |
| 8,696,559 | B2 | 4/2014 | Miles et al. |
| 8,753,271 | B1 | 6/2014 | Miles et al. |
| 8,764,649 | B2 | 7/2014 | Miles et al. |
| 8,827,902 | B2 | 9/2014 | Dietze, Jr. et al. |
| 8,968,363 | B2 | 3/2015 | Weiman et al. |
| 8,986,344 | B2 | 3/2015 | Sandhu |
| 8,992,425 | B2 | 3/2015 | Karpowicz et al. |
| 9,050,146 | B2 | 6/2015 | Woolley et al. |
| 9,084,591 | B2 | 7/2015 | Reglos et al. |
| 9,113,854 | B2 | 8/2015 | Ellman |
| 9,138,217 | B2 | 9/2015 | Smith et al. |
| 9,179,903 | B2 | 11/2015 | Cianfrani et al. |
| 9,357,909 | B2 | 6/2016 | Perez-Cruet et al. |
| 9,381,008 | B2 | 7/2016 | Thornburg |
| 9,386,916 | B2 | 7/2016 | Predick et al. |
| 9,408,596 | B2 | 8/2016 | Blain |
| 9,414,828 | B2 | 8/2016 | Abidin et al. |
| 9,468,405 | B2 | 10/2016 | Miles et al. |
| 9,486,133 | B2 | 11/2016 | Lee et al. |
| 9,549,723 | B2 | 1/2017 | Hynes et al. |
| 9,572,560 | B2 | 2/2017 | Mast et al. |
| 9,585,649 | B2 | 3/2017 | Blain et al. |
| 9,615,818 | B2 | 4/2017 | Baudouin et al. |
| 9,622,732 | B2 | 4/2017 | Martinelli et al. |
| 9,636,097 | B2 | 5/2017 | Bass |
| 9,649,101 | B2 | 5/2017 | Karpowicz et al. |
| 9,730,683 | B2 | 8/2017 | Reimels |
| 9,737,288 | B2 | 8/2017 | Karpowicz et al. |
| 9,795,370 | B2 | 10/2017 | O'Connell et al. |
| 9,795,371 | B2 | 10/2017 | Miles et al. |
| 9,826,966 | B2 | 11/2017 | Mast et al. |
| 9,918,709 | B2 | 3/2018 | Sandhu |
| 9,924,859 | B2 | 3/2018 | Lee et al. |
| 9,974,531 | B2 | 5/2018 | Miles et al. |
| 9,993,239 | B2 | 6/2018 | Karpowicz et al. |
| 10,039,539 | B2 | 8/2018 | Friedrich et al. |
| 10,070,852 | B2 | 9/2018 | Mast et al. |
| 10,076,320 | B2 | 9/2018 | Mast et al. |
| 10,149,671 | B2 | 12/2018 | Predick et al. |
| 10,154,781 | B2 | 12/2018 | Weiman |
| 10,172,515 | B2 | 1/2019 | Lee et al. |
| 10,172,652 | B2 | 1/2019 | Woolley et al. |
| 10,178,987 | B2 | 1/2019 | Predick et al. |
| 10,213,192 | B2 | 2/2019 | Capote |
| 10,213,193 | B2 | 2/2019 | Karpowicz et al. |
| 10,219,798 | B2 | 3/2019 | Capote |
| 10,238,375 | B2 | 3/2019 | O'Connell et al. |
| 10,245,015 | B2 | 4/2019 | Predick et al. |
| 10,278,686 | B2 | 5/2019 | Baudouin et al. |
| 10,278,786 | B2 | 5/2019 | Friedrich et al. |
| 10,285,680 | B2 | 5/2019 | Friedrich et al. |
| 10,299,777 | B2 | 5/2019 | Mast et al. |
| 10,357,233 | B2 | 7/2019 | Miles et al. |
| 10,426,450 | B2 | 10/2019 | Vogel et al. |
| 2005/0215863 | A1 | 9/2005 | Ravikumar et al. |
| 2006/0224044 | A1 | 10/2006 | Marchek et al. |
| 2007/0100212 | A1 | 5/2007 | Pimenta et al. |
| 2009/0024158 | A1 | 1/2009 | Viker |
| 2010/0174148 | A1 | 7/2010 | Miles et al. |
| 2012/0283521 | A1 | 11/2012 | Smith et al. |
| 2013/0317312 | A1 | 11/2013 | Eastlack et al. |
| 2016/0081681 | A1 | 3/2016 | Waugh et al. |
| 2016/0345952 | A1 | 12/2016 | Kucharzyk et al. |
| 2017/0035406 | A1 | 2/2017 | Abidin et al. |
| 2017/0215856 | A1 | 8/2017 | Martinelli et al. |
| 2018/0303473 | A1 | 10/2018 | Spann et al. |
| 2018/0344307 | A1 | 12/2018 | Hynes et al. |
| 2019/0021716 | A1 | 1/2019 | Waugh et al. |
| 2019/0082949 | A1 | 3/2019 | Weiman |
| 2019/0083081 | A1 | 3/2019 | Ortiz et al. |
| 2019/0125328 | A1 | 5/2019 | Blain |
| 2019/0133434 | A1 | 5/2019 | Lee et al. |
| 2019/0142480 | A1 | 5/2019 | Woolley et al. |
| 2019/0209155 | A1 | 7/2019 | Mast et al. |
| 2019/0216453 | A1 | 7/2019 | Predick et al. |
| 2019/0254650 | A1 | 8/2019 | Martinelli et al. |
| 2019/0274670 | A1 | 9/2019 | O'Connell et al. |
| 2019/0274671 | A1 | 9/2019 | Lauf et al. |
| 2019/0321022 | A1* | 10/2019 | Karpowicz ............ A61B 17/02 |
| 2019/0350573 | A1 | 11/2019 | Vogel et al. |

\* cited by examiner

TISSUE RETRACTOR

FIELD

The present technology is generally related to medical devices to assist a surgeon during treatment of musculoskeletal disorders, and more particularly to a surgical system and method for accessing a surgical site to facilitate treatment. More particularly, the present disclosure is directed to a surgical retractor system including a primary retractor assembly and a secondary retractor assembly that are configured for various approaches to the spine, including for example, anterior, lateral, and oblique surgical techniques.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, how-ever, may fail to relieve the symptoms associated with these disorders. Surgical treatment of these spinal disorders includes fusion, fixation, discectomy, laminectomy and implantable prosthetics. Surgical retractors may be employed during a surgical treatment to provide access and visualization of a surgical site. Such retractors space apart and support tissue and/or other anatomical structures to expose anatomical structures at the surgical site and/or provide a surgical pathway for the surgeon to the surgical site.

SUMMARY

This disclosure describes an adjustable surgical retractor system having a first surgical retractor assembly including at least two blades that can optionally be mated with a second surgical retractor assembly including at least two blades for enhanced configurability and variability over prior art retractor systems. Additionally, this disclosure describes a plurality of nested dilators having, for example, alternating circular cross sectional shapes and oval (ellipsis) cross sectional shapes that facilitate dilation of anatomical features in a controlled way, e.g., the fibers of the paraspinous muscle may be separated more gently by the oval cross sectional shape of the dilation tools.

The techniques of this disclosure generally relate to tissue retraction and dilation systems and methods that are directed to providing an enlarged surgical opening in a controlled manner. Disclosed tissue retraction systems may be highly customizable and include a primary retraction assembly having a pair of handles and a pair of blades that can be used independently on its own and/or in conjunction with a secondary retraction assembly that may couple to the primary retractor assembly and that also has either one or a pair of additional blades. The primary retraction assembly and secondary retraction assembly each may feature, for example, a plurality of pivoting members capable of independently inclining a corresponding blade.

In one aspect, the present disclosure provides a retractor system for enabling access to a surgical site. The retractor system may include a primary retractor assembly configured to open and close a first arm and a second arm along a first path of travel. The primary retractor assembly may include a handle assembly having first and second handles operably coupled to the first and second arms and configured to open and close the first and second arms, respectively, the first and second arms operably coupled to first and second pivoting members at a distal end thereof, respectively. The first and second pivoting members may be configured to operably couple to first and second blades, respectively. The primary retractor assembly may further include a first actuator and a second actuator configured to actuate the first and second pivoting members, respectively. The first and second pivoting members may be configured to independently angulate the first and second blades, respectively. The primary retractor assembly may further include a primary actuator configured to actuate a primary pinion gear mechanism operably coupled to the first and second handles and configured to open and close the first and second blades along the first path upon actuation of the primary actuator. The retractor system may further include a secondary retractor assembly configured to couple and uncouple with the primary retractor assembly and independently extend and contract a third arm. The secondary retractor assembly may include a first channel for operably retaining the third arm therein, the first channel defining a second path of travel, and the third arm may be configured to travel along the second path. The secondary retractor assembly may further include a third actuator disposed adjacent the first channel and operably configured to extend and contract the third arm via a first pinion gear mechanism. The third arm may be operably coupled to a third pivoting member at a distal end thereof, and the third pivoting member may be configured to operably couple and uncouple with a third blade. The secondary retractor assembly may further include a fifth actuator configured to actuate the third pivoting member, the third pivoting member being configured to independently angulate the third blade, upon actuation of the fifth actuator.

In another aspect, the secondary retractor assembly may be further configured to couple and uncouple from the primary retractor assembly via a first recessed key portion and a second recessed key portion disposed on the first and second arms, respectively, and a turnkey projecting from a central portion of the primary retractor assembly through a central aperture of the secondary retractor assembly.

In another aspect, the primary retractor assembly may be further configured to independently open and close the first arm along the first path upon movement of the first handle and independently open and close the second arm along the first path upon movement of the second handle.

In another aspect, the primary pinion gear mechanism is operably coupled to the first and second handles that is configured to provide a controlled mechanical advantage to open and close the first and second arms along the first path upon actuation of the primary actuator.

In another aspect, the secondary retractor assembly is further configured to extend and withdraw or translate away from the operative corridor a fourth arm. The secondary retractor assembly may further include a second channel for operably retaining a fourth arm therein, and the second channel may define a third path of travel and the fourth arm may be configured to travel along the third path. The secondary retractor assembly may further include a fourth actuator disposed adjacent the second channel and operably configured to extend and contract the fourth arm via a second pinion gear mechanism and the fourth arm may be operably coupled to a fourth pivoting member at a distal end thereof, and be configured to operably couple and uncouple with a fourth blade. The secondary retractor assembly may further include a sixth actuator configured to actuate the fourth pivoting member the fourth pivoting member being configured to independently angulate the fourth blade upon actuation of the sixth actuator.

In another aspect, the first and second pivoting members may each further comprise a corresponding pin and socket mechanism and a corresponding blade attachment mechanism having a dovetail groove configured to engage a corresponding one of the first blade and second blade, respectively, and the third and fourth pivoting members each further comprise a corresponding pin and socket mechanism and a corresponding blade attachment mechanism having a dovetail groove configured to engage a corresponding one of the third blade and fourth blade, respectively.

In another aspect, the primary retractor assembly may further include a primary retention lever configured to control opening and closing of the first and second arms.

In another aspect, the primary retention lever engages a rack portion fixedly coupled to the second arm to thereby control opening and closing of the first and second arms.

In another aspect, the secondary retractor assembly further comprises a first retention lever configured to engage the third arm to control extension and contraction of the third arm and a second retention lever configured to engage the fourth arm to control extension and contraction of the fourth arm.

In another aspect, the first, second, third, and fourth blades are each configured to operably couple to a corresponding first, second, third, and fourth shim.

In another aspect, least one of the first, second, third, and fourth blades is configured to surround at least a portion of the at least one dilator and may contact an outside surface of the at least one dilator.

In another aspect, at least one of the first, second, third, and fourth blades is configured to surround at least a portion of a set of nested dilators and may contact an outside surface of an outermost dilator of the set of nested dilators.

In another aspect, at least one of the first, second, third, and fourth blades is configured to surround and contact at least a portion of an outermost one of a set of nested dilators. The set of nested dilators may further include: a first dilator having a circular cross section, a second dilator having an ellipsis shaped cross section and surrounding the first dilator, a third dilator having a circular cross section and surrounding the second dilator, and a fourth dilator having an ellipsis shaped cross section and surrounding the third dilator. Additionally, the first dilator may be an innermost dilator and the fourth dilator may be an outermost dilator.

In another aspect, the first channel may have an arcuate shape, the third arm may have a corresponding arcuate shape, and the arcuate shape of the first channel may define the second path. The second channel may have an arcuate shape, the fourth arm may have a corresponding arcuate shape, and the arcuate shape of the second channel may define the third path. Additionally, a radius of curvature of the first path may be greater than a radius of curvature of the second path and a radius of curvature of the third path.

In another aspect, the primary retractor assembly may further include at least one table mounting portion configured to mount to a table thereby fixedly coupling the retractor system stably to the table.

In one aspect, a method for enabling access to a surgical site, may be disclosed. The method may include the steps of providing a primary retractor assembly and opening at least one of the first arm and the second arm along the first path. The method may also include the step of closing at least one of the first arm and the second arm along the first path.

In another aspect, disclosed methods may include providing a secondary retractor assembly and extending, independently, at least one of the third arm along the second path and the fourth arm along the third path. Additionally, disclosed methods may include contracting, independently, at least one of the third arm along the second path and the fourth arm along the third path.

In another aspect, disclosed methods may include independently angulating at least one blade chosen from the first blade, second blade, third blade, and fourth blade.

In another aspect, disclosed methods may include providing a set of nested dilators, and sequentially dilating the paraspinous muscle before the steps of: opening/closing at least one of the first arm and the second arm along the first path.

In another aspect, a retractor system for enabling access to a surgical site, is disclosed. The retractor system may include a primary retractor assembly configured to open and close a first arm and a second arm along a first path of travel. The primary retractor assembly may include a handle assembly having first and second handles operably coupled to the first and second arms and configured to open and close the first and second arms independently upon opening and closing of the first and second handles. The first and second arms may be operably coupled to first and second pivoting members at a distal end thereof, respectively, and the first and second pivoting members may be configured to operably couple to first and second blades, respectively. The primary retractor system may further include a first actuator and a second actuator configured to actuate the first and second pivoting members, respectively. The first and second pivoting members may be configured to independently angulate the first and second blades upon actuation of the first and second actuators, respectively. The first and second pivoting members may each include a corresponding pin and socket mechanism and a corresponding blade attachment mechanism. The corresponding blade attachment mechanism may include a dovetail groove configured to engage a corresponding one of the first blade and second blade, respectively. The primary retractor system may further include a primary actuator configured to actuate a primary pinion gear mechanism comprising a primary gear, a secondary gear, and a tertiary gear, the primary pinion gear mechanism being operably coupled to the first and second handles and configured to provide a controlled mechanical advantage to simultaneously open and close the first and second arms along the first path upon actuation of the primary actuator, and a primary retention lever configured to control opening and closing of the first and second arms. The retractor system may further include a secondary retractor assembly configured to couple and uncouple with the primary retractor assembly and independently extend and contract a third arm and a fourth arm, respectively. The secondary retractor assembly may further include a first arcuate channel for operably retaining a third arm therein and a second arcuate channel for operably retaining a fourth arm therein, the first arcuate channel may define a second arcuate path of travel and the second arcuate channel may define a third arcuate path of travel. The third arm may be configured to travel along the second path and the fourth arm may be configured to travel along the third path. The secondary retractor assembly may further include a third actuator disposed adjacent the first channel and operably configured to extend and contract the third arm via a first pinion gear mechanism and a fourth actuator disposed adjacent the second channel and operably configured to extend and contract the fourth arm via a second pinion gear mechanism.

The third and fourth arms may be operably coupled to third and fourth pivoting members at a distal end thereof, respectively, and the third and fourth pivoting members may be configured to operably couple and uncouple with third and fourth blades, respectively. The secondary retractor system may further include fifth and sixth actuators configured to actuate the third and fourth pivoting members, respectively, and the third and fourth pivoting members may be configured to independently angulate the third and fourth blades, respectively, upon actuation of the fifth and sixth actuators, respectively. The third and fourth pivoting members may each include a corresponding pin and socket mechanism and a corresponding blade attachment mechanism. Each corresponding blade attachment mechanism may include a dovetail groove that is configured to engage a corresponding one of the third blade and fourth blade. The secondary retraction assembly may further include a first retention lever configured to engage the third arm to control extension and contraction of the third arm and a second retention lever configured to engage the fourth arm to control extension and contraction of the fourth arm.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In one aspect, exemplary embodiments describe a retractor system 100 for use with anterior, lateral, and oblique surgical techniques. At least one use of retractor system 100 is to assist in the preparation of a surgical site to enable a surgeon to access a space between vertebrae of patient's spine. The retractor system 100 may assist a surgeon in accessing a space between vertebrae by enabling highly controlled dilation of the paraspinous muscles with a set of nested dilators and retraction of the various fibers and tissues at the surgical site with the use of a plurality of independently movable and inclinable blades.

Figure 1:
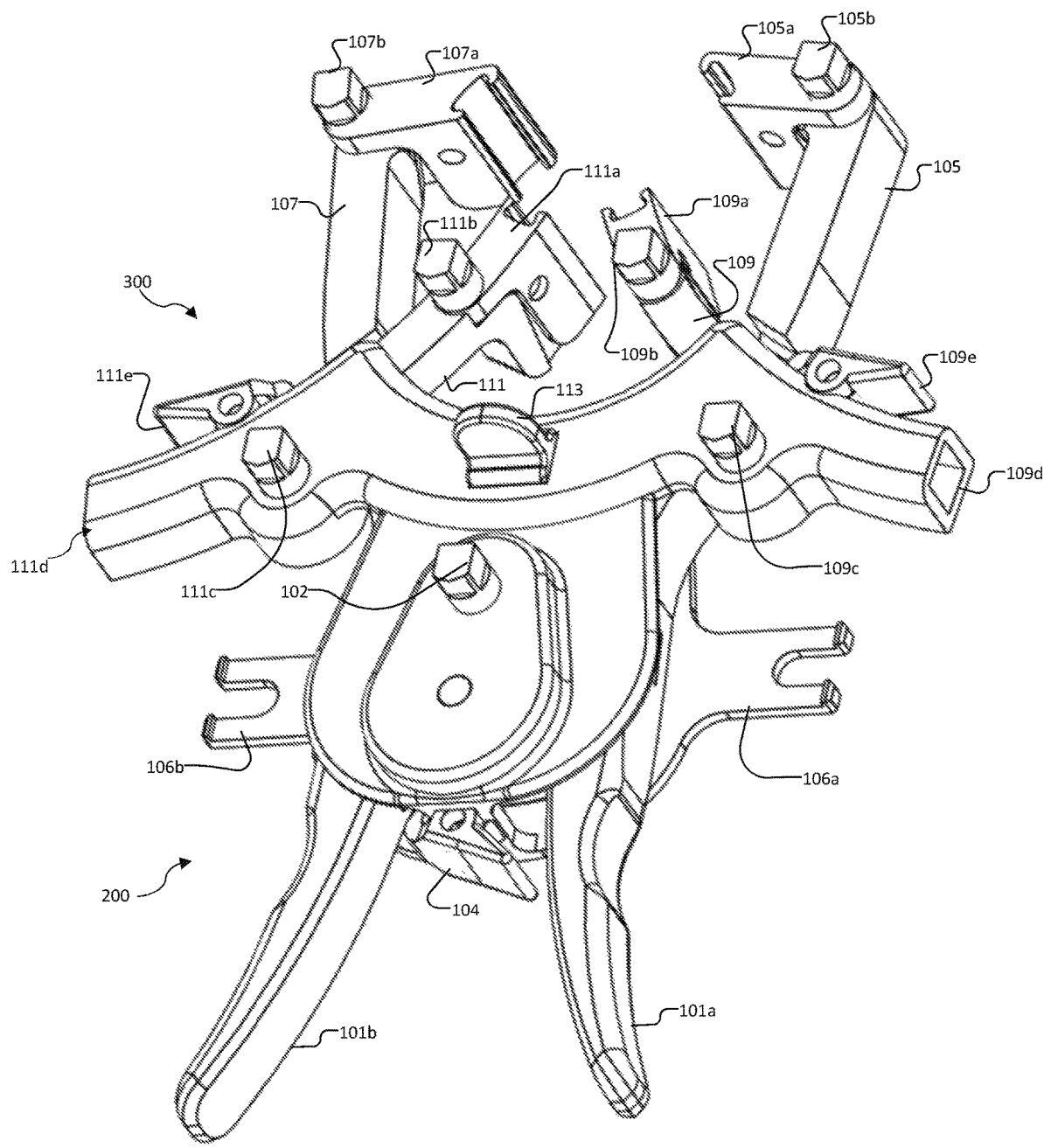
FIG. 1 is a perspective view of an exemplary embodiment of a retractor system including a primary retractor assembly and a secondary retractor assembly in accordance with the principles of the disclosure.

Referring generally to FIGS. 1-8 exemplary retractor systems for enabling access to a surgical site are disclosed. FIG. 1 is a perspective view of an exemplary embodiment of a retractor system 100 including a primary retractor assembly 200 and a secondary retractor assembly 300 in accordance with the principles of the disclosure. Retractor system 100 is highly customizable and modular. For example, the primary retractor assembly 200 may be used as a standalone retractor system without the use of secondary retractor assembly 300. Secondary retractor assembly 300 is configured to couple and uncouple on as needed basis with the primary retractor assembly 200. Additionally, secondary retractor assembly 300 can use one arm or two arms on an as needed basis with each arm having a corresponding blade.

Exemplary embodiments may include a primary retractor assembly 200 configured to open and close a first arm 105 and a second arm 107 along a first path of travel. The first path may be an arcuate path or segment defined by the length and geometry of the arms 105 and 107 and a handle pivoting mechanism 101c (see FIG. 8) configured to enable first handle 101a and second handle 101b to open and close. Other paths of travel are contemplated depending upon the geometry of the arms 105, 107 and the relative location of the handle pivoting mechanism 101c. The primary retractor assembly 200 may include a handle assembly having first and second handles 101a, 101b that are operably coupled to the first and second arms 105, 107 and configured to open and close the first and second arms 105, 107. For example, the first handle 101a may be coupled to the first arm 105 and the second handle 101b may be coupled to the second arm 107. The first and second arms 105, 107 may be operably coupled to first and second pivoting members 105a, 107a at a distal end thereof, respectively. The first and second pivoting members 105a, 107a may be configured to operably couple to first and second blades, 205, 207 (see FIG. 2), respectively, by a corresponding blade attachment mechanism as will be explained in more detail below during the discussion of FIGS. 9-13B.

In the exemplary embodiment, a first actuator 105b and a second actuator 107b are configured to adjust the angulation of first blade 205 and second blade 207, respectively. For example, the first actuator 105b may be configured to actuate the first pivoting member 105a to adjust the angulation of first blade 205 with respect to the first arm 105. Similarly, the second actuator 107b may be configured to actuate the second pivoting member 107a to adjust the angulation of second blade 207 with respect to second arm 107. In the exemplary embodiment, the first pivoting member 105a may be configured to independently adjust the angulation of first blade 205 with respect to the first arm 105 upon actuation of the first actuator 105b. Similarly, the second pivoting member 107a may be configured to independently adjust the angulation of the second blade 207 with respect to the second arm 107 upon actuation of the second actuator 107b. In disclosed embodiments, the first and second pivoting members 105a, 107a may each include a corresponding pin and socket mechanism enabling the pivoting members to pivot on a pin aperture 199 (see, e.g., FIG. 8). Additionally, the first and second pivoting members 105a, 107a may each include a corresponding blade attachment mechanism at a distal end thereof which will be explained in more detail below when discussing FIGS. 9-13.

In the exemplary embodiment, the primary retractor assembly 200 may include a primary actuator 102 that is configured to actuate a primary pinion gear mechanism 210 (see FIG. 7) to provide a precise and controlled mechanical advantage to open and close the first arm 105 and second arm 107. For example, the primary pinion gear mechanism 210 may include a primary pinion gear 210a fixedly coupled to the primary actuator 102 such that the primary actuator 102 may rotationally translate the primary pinion gear 210a. The primary pinion gear 210a may be engaged with the secondary pinion gear 210b, e.g., the primary pinion gear 210a and secondary pinion gear 210b may be toothed gears that are meshed with one another at a contact location (not illustrated). Furthermore, secondary pinion gear 210b may be fixedly coupled to tertiary pinion gear 210c which may be axially aligned with secondary pinion gear 210b and disposed directly beneath secondary pinion gear 210b (see FIG. 8). For example, secondary pinion gear 210b may share an axis of rotation with tertiary pinion gear 210c and secondary pinion gear 210b may be relatively larger in diameter than tertiary pinion gear 210c. This arrangement may resemble a two stage gear box or the like that allows for an increase in applied torque. In other embodiments, primary pinion gear mechanism 210 may be any other similar planetary gear system as would be understood by a person having ordinary skill in the relevant art. For example, those with skill in the relevant art will readily recognize that the particular diameter, tooth sizing, and tooth spacing of the primary pinion gear 210a relative to the particular diameter, tooth sizing, and tooth spacing of the secondary pinion gear 210b relative to tertiary pinion gear 210c may control the amount of force (mechanical advantage or torque) that is applied to open and close the first and second arms 105, 107.

Figure 8:
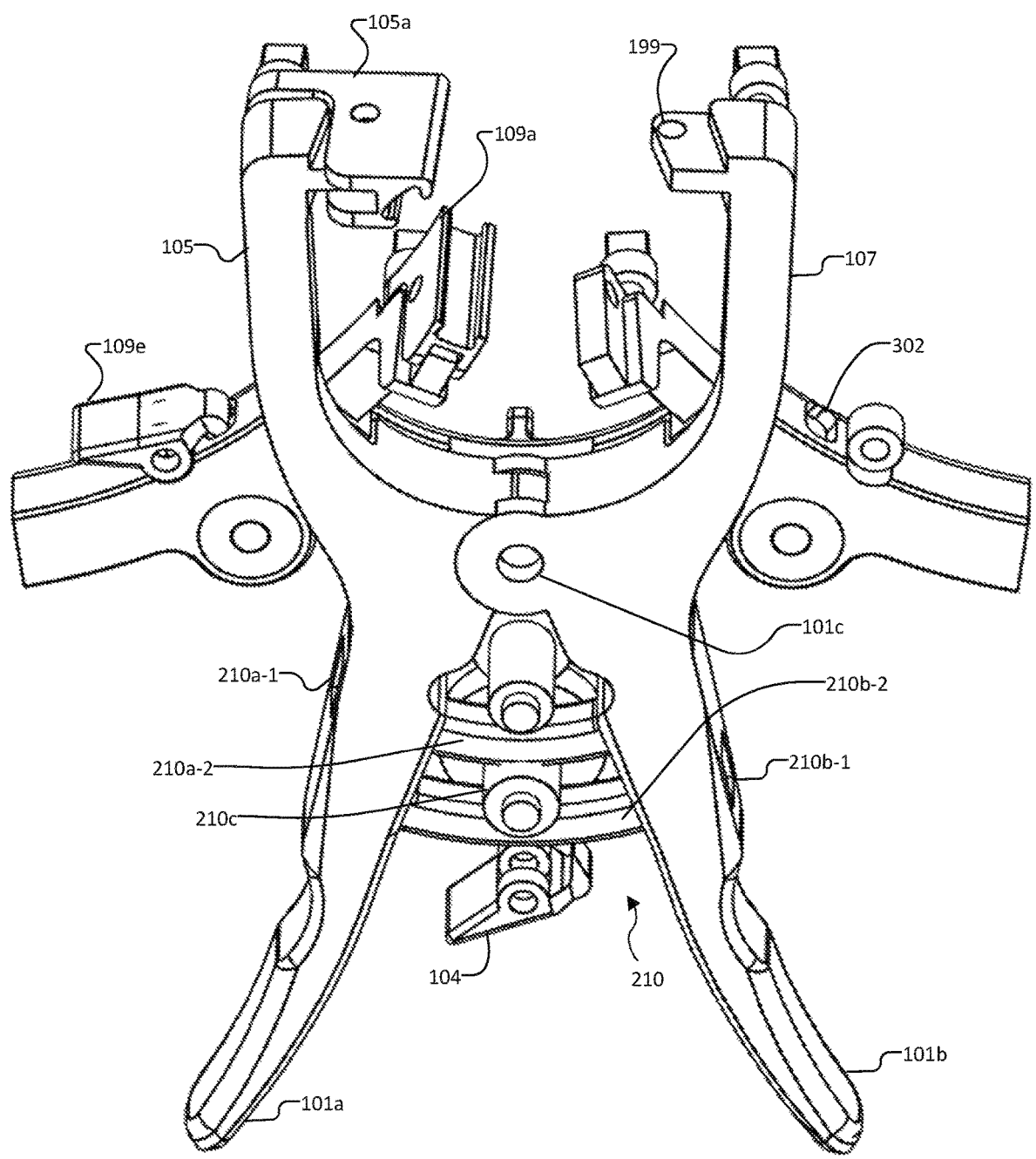
FIG. 8 is an alternate cutaway view of the retractor system of FIG. 1 in accordance with the principles of the disclosure.

In the exemplary embodiment of FIG. 8, tertiary pinion gear 210c may be meshed with a first curved rack portion 210a-2 and a second curved rack portion 210b-2 disposed opposite the first curved rack portion 210a-2. First curved rack portion 210a-2 may be fixedly coupled to second arm 101b and second curved rack portion 210b-2 may be fixedly coupled to first arm 101a. Each of curved rack portions 210a-2 and 210b-2 may feature a plurality of teeth extending along the curved body thereof and facing tertiary pinion gear 210c. The first curved rack portion 210a-2 and second curved rack portion 210b-2 may be meshed with the teeth of tertiary pinion gear 210c on opposite sides of tertiary pinion gear 210c. In this way, when primary actuator 102 is rotated, primary pinion gear 210a rotates which in turn rotates secondary pinion gear 210b and tertiary pinion gear 210c. In turn, tertiary pinion gear 210c engages teeth on each of curved rack portions 210a-2 and 210b-2 and causes handles 101a, 101b to open or close. In the disclosed embodiment, when tertiary pinion gear 210c applies force to first curved rack portion 210a-2, the first curved rack portion 210a-2 may extend through first handle 101a at a corresponding first handle aperture 210a-1. Similarly, when tertiary pinion gear 210c applies force to second curved rack portion 210b-2, the second curved rack portion 210b-2 may extend through second handle 101b at a corresponding second handle aperture 210b-1.

In disclosed embodiments, the primary pinion gear mechanism 210 may be operably coupled to the first and second handles 101a, 101b and configured to simultaneously open and close the first and second arms 105, 107 along a first path of travel. For example, the primary actuator 102 may rotationally translate the primary pinion gear mechanism 210 in a clockwise direction which in turn rotationally translates the first arm 105 and second arm 107 such that they move away from one another, i.e., they open as explained above. Likewise, the primary actuator 102 may rotationally translate the primary pinion gear mechanism 210 in a counter clockwise direction which in turn rotationally translates the first arm 105 and second arm 107 such that they move towards one another, i.e., they close as explained above. Also as explained above, the particular diameter of primary, secondary, and tertiary pinion gears 210a, 210b, and 210c may be adjusted to provide the desired amount of mechanical advantage or torque to open and close first and second arms 101a, 101b.

In disclosed embodiments, primary retractor assembly 200 may include a primary retention lever 104 disposed between the first and second handles 101a, 101b that is configured to engage the primary retractor assembly 200 to control opening and closing of the first and second arms 105, 107 and thereby retain the first and second arms 105, 107 in a specific position. In the disclosed embodiment, primary retention lever 104 may frictionally engage curved rack portion 210b-2 to control opening and closing of the first and second arms. In other embodiments, the primary retention lever 104 may engage the primary pinion gear mechanism 210 at an outside portion of the circumference of the primary pinion gear 210a (see FIG. 7) to thereby control and/or prevent rotation of the primary pinion gear 210a. For example, the primary retention lever 104 may lock the primary pinion gear mechanism 210 in place to control opening and closing of the first and second arms. In some embodiments, the primary retention lever 104 may have a biasing element (not illustrated) that causes the primary retention lever 104 to naturally urge an angled tip portion of the body of the primary retention lever 104 against a portion of the primary pinion gear mechanism 210. For example, a spring may naturally urge an angled tip portion of primary retention lever 104 to engage with a toothed portion of secondary pinion gear 210b. Additionally, the primary retention lever 104 may be moved from an engagement position where primary retention lever 104 is in direct contact with the primary pinion gear mechanism 210 to a disengaged position where primary retention lever 104 is not engaged with the primary pinion gear mechanism 210. For example, an end user such as a surgeon may depress primary retention lever 104 with their thumb to toggle primary retention lever 104 between the engaged position and the disengaged position. Furthermore, some embodiments may have a toggle feature (not illustrated) for maintaining the primary retention lever 104 in either of the engaged or disengaged positions.

In disclosed embodiments, the primary retractor assembly 200 may include a first table mount portion 106a disposed adjacent the first handle 101a and coupled to a body 200a (see FIG. 5) or housing of the primary retractor assembly 200. Similarly, the primary retractor assembly 200 may include a second table mount portion 106b disposed adjacent the second handle 101b and coupled to the body or housing of the primary retractor assembly 200. The first and second table mount portions 106a, 106b may each be attached to a surgical table (not illustrated) for fixing the primary retractor assembly 200 (and/or the retractor system 100) in a fixed location in three dimensional space. In example embodiments, the primary retractor assembly 200 may be attached to a surgical table by at least one of the first and second table mount portions 106a, 106b or by both.

At least one advantage of securing the primary retractor assembly 200 to a surgical table may be for enhanced stability and the even transfer of resultant forces from the primary actuator 102 through the first and second arms 105, 107 to the first and second blades 205, 207 and vice versa. For example, when the primary retractor assembly 200 is fixed to the surgical table and the primary actuator 102 is translated to open the first and second arms 105, 107 the primary pinion gear mechanism 210 may apply a precise controlled amount of force to open the first and second arms 105, 107 to thereby gently retract the tissue of a patient in a controlled manner. Additionally, when the primary retractor assembly 200 is fixed to the surgical table, it may be easier for an end user to independently move only one of the handles 101a, 101b with respect to the surgical table. When moving only one of the handles 101a, 101b the corresponding arm 105, 107 may move relative to the other. This scenario and functionality may assist a surgeon with precise surgical techniques where it may be desirable to independently move either of the first and second arms 105, 107 along the first path of travel independently with respect to the other.

Disclosed embodiments described above may be configured to independently open and close the first arm 105 along the first path of travel by movement of the first handle 101a relative to the second handle 101b and independently open and close the second arm 107 along the first path of travel by movement of the second handle 101b relative to the first handle 101a. Additionally, because the primary pinion gear mechanism 210 includes a primary gear 210a and a secondary gear 210b operably coupled to the first and second handles 101a, 101b disclosed embodiments may be configured to provide a controlled mechanical advantage to open and close the first and second arms 105, 107 along the first path upon actuation of the primary actuator 102.

Figure 2:
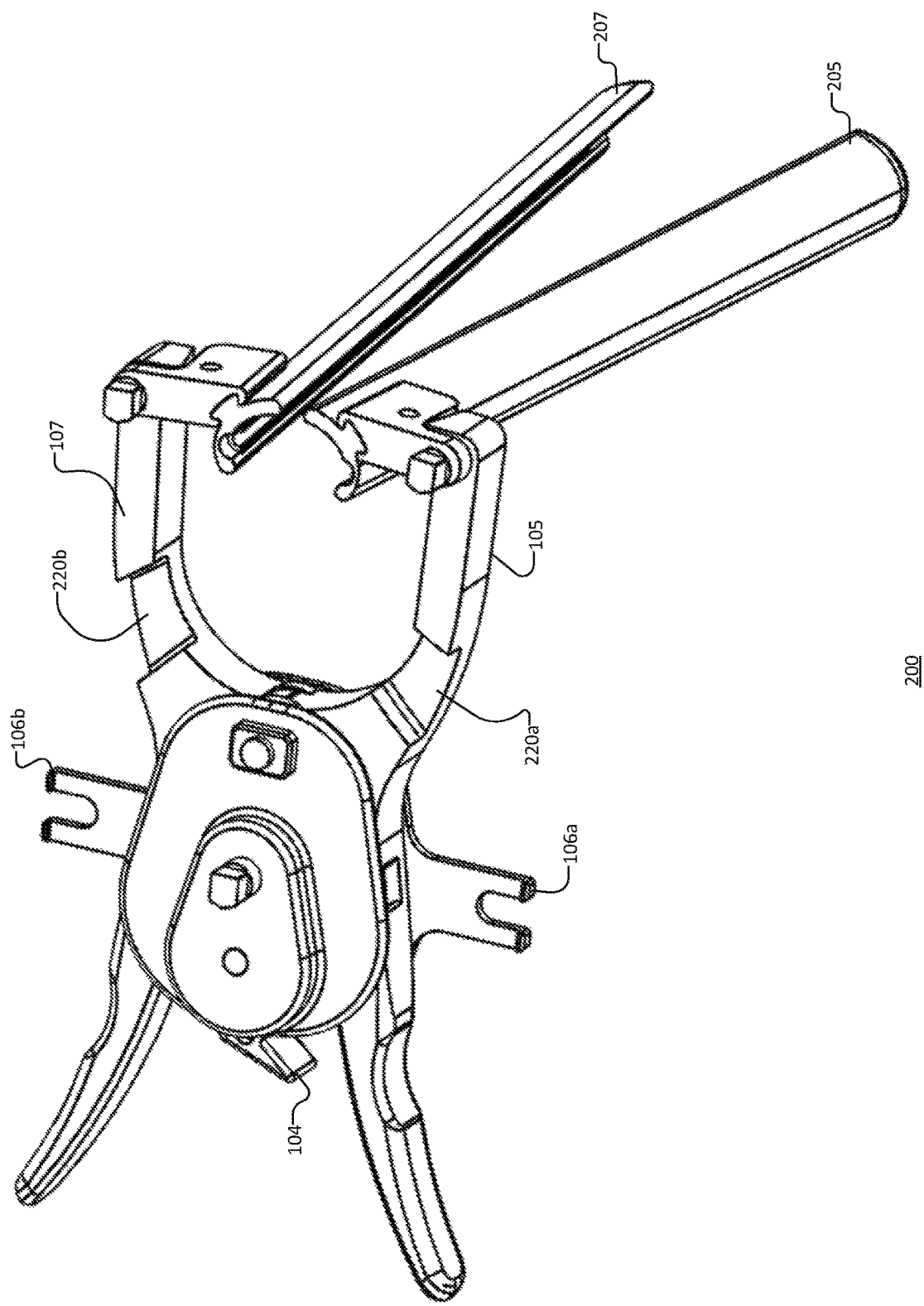
FIG. 2 is a perspective view of the primary retractor assembly of FIG. 1 in accordance with the principles of the disclosure.
Figure 3:
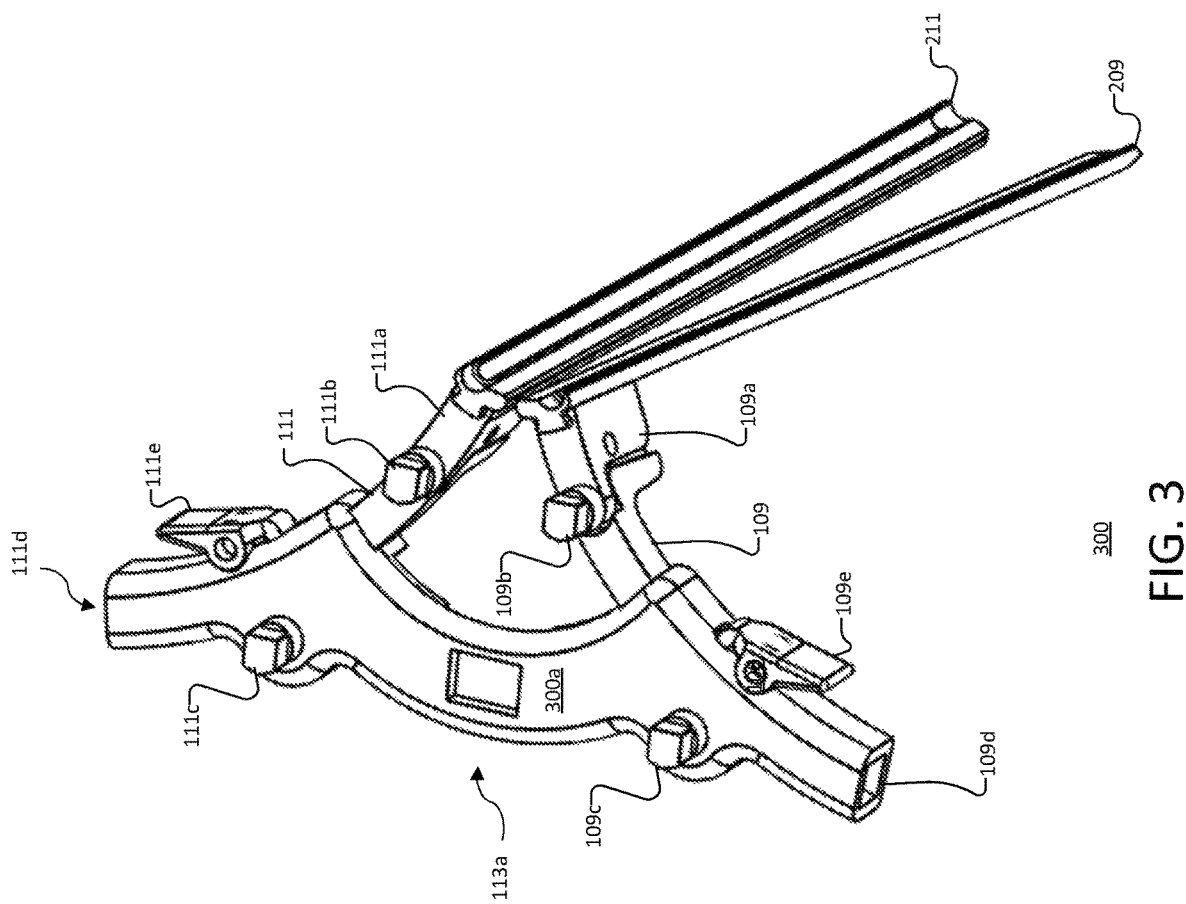
FIG. 3 is a perspective view of the secondary retractor assembly of FIG. 1 in accordance with the principles of the disclosure.
Figure 4:
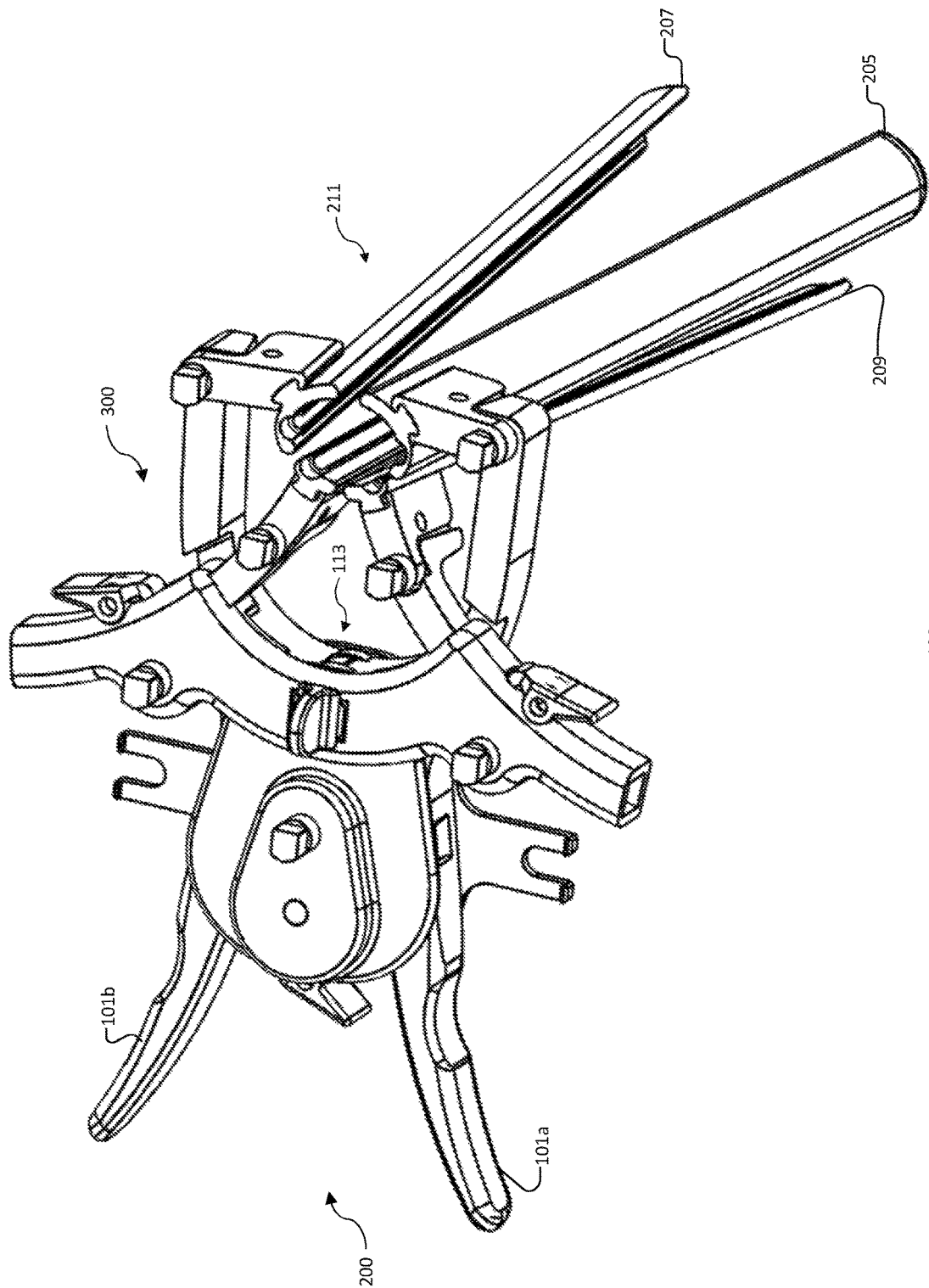
FIG. 4 is a perspective view of the retractor system of FIG. 1 including a plurality of blades in accordance with the principles of the disclosure.
Figure 5:
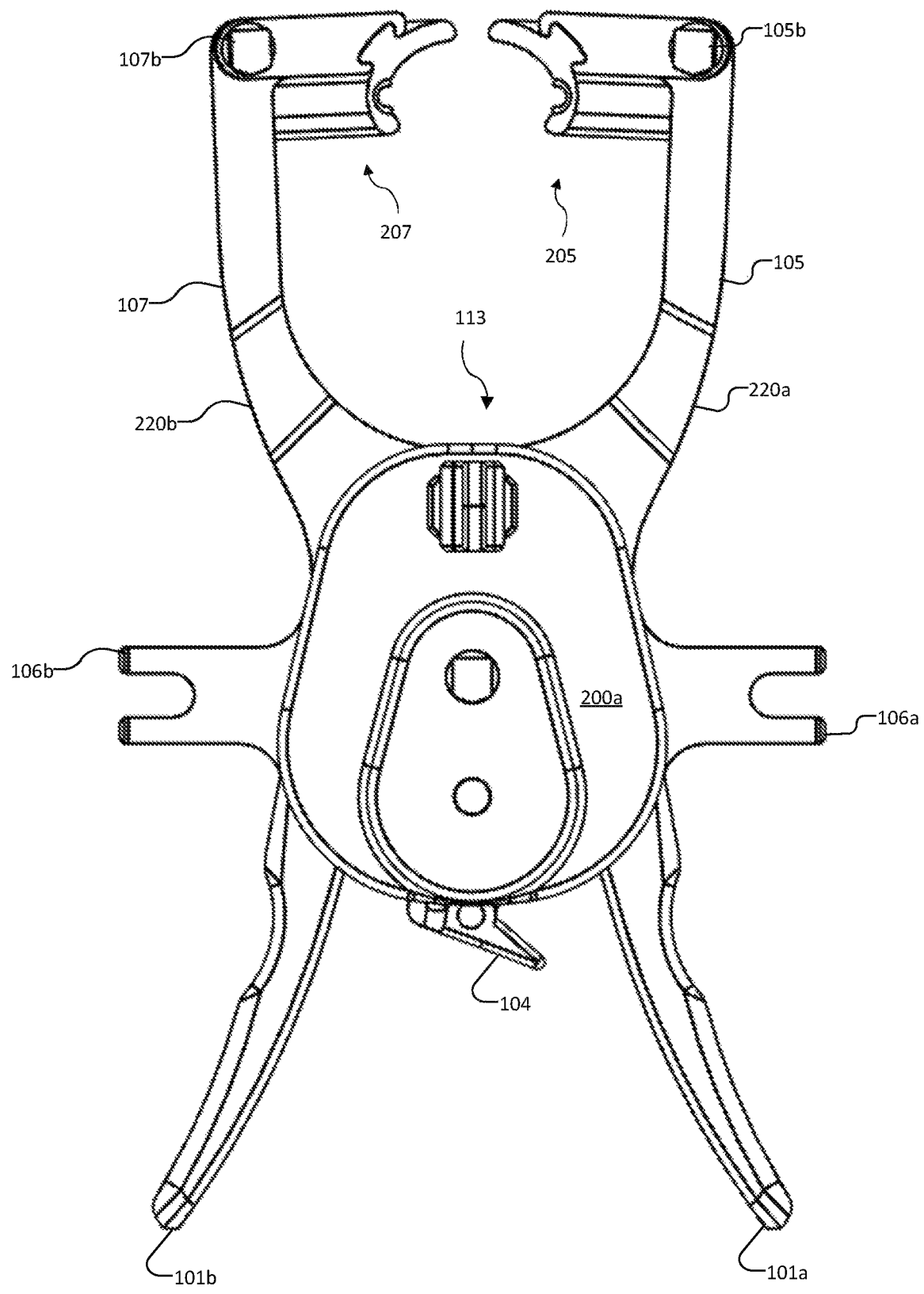
FIG. 5 is a top down view of the primary retractor assembly of FIG. 2 in accordance with the principles of the disclosure.
Figure 6:
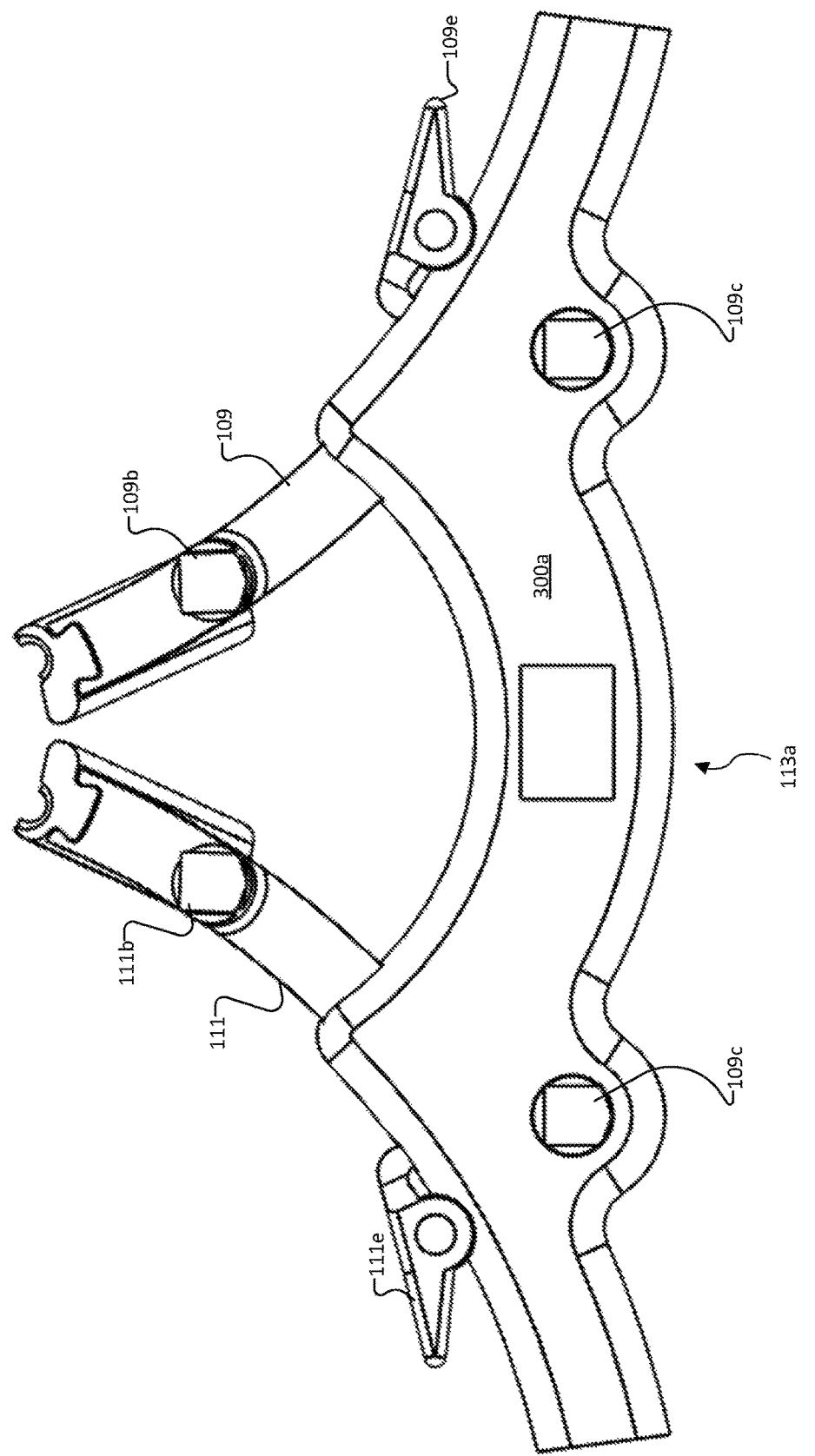
FIG. 6 is a top down view of the secondary retractor assembly of FIG. 3 in accordance with the principles of the disclosure.

In accordance with disclosed embodiments, a secondary retractor assembly 300 may be configured to couple and uncouple from the primary retractor assembly 200 via a first recessed key portion 220a disposed on the first arm 105 and a second recessed key portion 220b disposed on the second arm 107 (see FIG. 2). Each of recessed key portions 220a, 220b may include a groove having a geometry that facilitates engagement of the primary retractor assembly 200 with the secondary retractor assembly 300 while also operably allowing the opening and closing of arms 105, 107. For example, the secondary retractor assembly 300 may have a corresponding outdent (e.g., dovetail) on an underside thereof configured to mate with an indent (e.g., dovetail groove) of the primary retractor assembly 200. Additionally, secondary retractor assembly 300 may be fixed to primary retractor assembly 200 by turnkey 113. Turnkey 113 may project from a central portion of the primary retractor assembly 200 through a central aperture 113a (see FIG. 6) of the secondary retractor assembly 300. In a first position, turnkey 113 may urge the primary retractor assembly 200 and secondary retractor assembly 300 towards each other and maintain direct contact to fixedly engage them to one another. Conversely, in a second position, turnkey 113 may be rotated such that turnkey 113 is aligned with central aperture 113a and therefore has no bearing surface to urge the primary retractor assembly 200 and secondary retractor assembly 300 towards each other. Thus, in the second position the primary retractor assembly 200 and secondary retractor assembly 300 may be disengaged from one another. Other embodiments may use alternate means to securely engage the primary retractor assembly 200 with the secondary retractor assembly 300, e.g., as fasteners, hexagonal grooves, channel locks, magnets, etc. provided that the primary retractor assembly 200 and the secondary retractor assembly 300 are securely engaged with one another such that resultant forces acting on the retractor system 100 may transfer between primary retractor assembly 200 and secondary retractor assembly 300 and also by extension to a surgical table via table mount portions 106a and/or 106b.

Secondary retractor assembly 300 may have a body portion 300a generally defining a first channel 109d and a second channel 111d. Secondary retractor assembly 300 may be configured to independently extend and contract a third arm 109 and a fourth arm 111, respectively. Although two channels 109d, 111d and two arms 109, 111 are illustrated it is contemplated that secondary retractor assembly 300 may have any number of suitable channels and arms. Additionally, it is contemplated that only a single arm, e.g., third arm 109 or fourth arm 111 will be provided in some surgical settings.

In disclosed embodiments, the secondary retractor assembly 300 may include a first channel 109d having a curved or arcuate shape for operably retaining third arm 109 therein where third arm 109 has a corresponding curved or arcuate shape. The third arm 109 may be configured to extend outwards from first channel 109d and contract within first channel 109d Similarly, secondary retractor assembly 300 may include a second channel 111d having a curved or arcuate shape for operably retaining fourth arm 111 therein where fourth arm 111 has a corresponding curved or arcuate shape. The fourth arm 111 may be configured to extend outwards from first channel 111d and contract within second channel 111d. The geometry of the first channel 109d and third arm 109 may define a second path of travel, e.g., an arcuate path of travel defined by the arcuate shapes of the first channel 109d and third arm 109. Similarly, the geometry of the second channel 111d and fourth arm 111 may define a third path of travel, e.g., an arcuate path of travel defined by the arcuate shapes of the second channel 111d and fourth arm 111.

In disclosed embodiments, the secondary retractor assembly 300 may include a third actuator 109c operably disposed adjacent the first channel 109d and operably configured to extend and contract the third arm 109 via a pinion gear mechanism (not illustrated) having the same or similar components as primary pinion gear mechanism 210 of primary retractor assembly 200. For example, a toothed pinion P1 (see FIG. 7) may be coupled to actuator 109c and may operably engage a corresponding rack portion (not illustrated) on an adjacent surface of arm 109 to linearly translate, e.g., curvo-linear, third arm 109 forward and backward, i.e., extend and withdraw or translate away from the operative corridor. Similarly, the secondary retractor assembly 300 may include a fourth actuator 111c operably disposed adjacent the second channel 111d and operably configured to extend and contract the fourth arm 111 via a pinion gear mechanism (not illustrated) having the same or similar components as primary pinion gear mechanism 210 of primary retractor assembly 200. For example, a toothed pinion P2 (see FIG. 7) may be coupled to actuator 111c and may operably engage a corresponding rack portion (not illustrated) on an adjacent surface of arm 111 to linearly translate, e.g., curvo-linear, fourth arm 111 forward and backward, i.e., extend and withdraw or translate away from the operative corridor. For example, actuator 109c may rotationally translate P1 in a clockwise direction which in turn linearly translates the third arm 109 arm such that it extends outward from channel 109d. Similarly, actuator 109c may rotationally translate P1 in a counter clockwise direction which in turn linearly translates the third arm 109 arm such that it contracts inward into channel 109d. Likewise, actuator 111c may rotationally translate P2 in a clockwise direction which in turn linearly translates the fourth arm 111 arm such that it extends outward from channel 111d. Similarly, actuator 111c may rotationally translate P2 in a counter clockwise direction which in turn linearly translates the fourth arm 111 such that it contracts inward into channel 109d. Accordingly, in disclosed embodiments, the third arm 109 is configured to independently extend and contract along a second path of travel upon actuation of the third actuator 109c, and the fourth arm 111 is configured to independently extend and contract along a third path of travel upon actuation of the fourth actuator 111c.

In disclosed embodiments, the third and fourth arms 109, 111 may be operably coupled to third and fourth pivoting members 109a, 111a at a distal end thereof, respectively. The third and fourth pivoting members 109a, 111a may be configured to operably couple to third and fourth blades 209, 211, respectively (see FIG. 3) by a corresponding blade attachment mechanism as will be explained in more detail below during the discussion of FIGS. 9-13B. In the exemplary embodiment, a fifth actuator 109b and a sixth actuator 111b are configured to adjust the angulation of third blade 209 and fourth blade 211, respectively. For example, the fifth actuator 109b may be configured to actuate the third pivoting member 109a to adjust the angulation of third blade 209 with respect to the third arm 109. Similarly, the sixth actuator 211b may be configured to actuate the fourth pivoting member 211a to adjust the angulation of fourth blade 211 with respect to fourth arm 111. In the exemplary embodiment, the third pivoting member 109a may be configured to independently adjust the angulation of third blade 209 with respect to third arm 109 upon actuation of the fifth actuator 109b. Similarly, the fourth pivoting member 211a may be configured to independently adjust the angulation of fourth blade 211 with respect to the fourth arm 111 upon actuation of the fourth actuator 111b.

In disclosed embodiments, the third and fourth pivoting members 209a, 211a may each include a corresponding pin and socket mechanism enabling the pivoting members 209a, 211a to pivot on a pin disposed in a corresponding pin aperture 199 (see, e.g., FIG. 8). Additionally, the third and fourth pivoting members 209a, 211a may each include a corresponding blade attachment mechanism at a distal end thereof which will be explained in more detail below when discussing FIGS. 9-13.

In disclosed embodiments, the secondary retractor assembly 300 may include a first retention lever 109e configured to engage the third arm 109 to control extension and contraction of the third arm 109 along the second path of travel and a second retention lever 111e configured to engage the fourth arm 111 to control extension and contraction of the fourth arm 111 along the third path of travel. First and second retention levers 109e, 111e may have the same or similar components as described above with respect to primary retention lever 104.

First retention lever 109e and second retention lever 111e may frictionally engage with the third arm 109 and fourth arm 111, respectively, to control and/or prevent the extension and contraction of the third arm 109 and fourth arm 111. For example, first retention lever 109e and second retention lever 111e may engage with a rack portion on an outside adjacent surface of the third arm 109 and fourth arm 111, respectively, through an aperture 302 (see FIG. 8) projecting through a portion of channels 109d, 111d, respectively. In some embodiments, first and second retention levers 109e, 111e may include a biasing element having the same or similar components as explained above with respect to primary retention lever 104. In some embodiments, first retention lever 109e may engage a corresponding pinion gear mechanism operably associated with actuator 109c to thereby control and/or prevent rotation of the corresponding pinion gear mechanism. Similarly, second retention lever 111e may engage a corresponding pinion gear mechanism operably associated with actuator 109c to thereby control and/or prevent rotation of the corresponding pinion gear mechanism.

Referring generally to FIGS. 1, 7, and 9-11 the pivoting members 105a, 107a, 109a, and 111a may each include the same or similar components and features. For example, pivoting members 105a, 107a, 109a, and 111a may each include a corresponding pin and socket mechanism. The pin and socket mechanism of pivoting members 105a, 107a, 109a, and 111a may be adjustable by way of actuators 105b, 107b, 109b, and 111b such that an inclination of pivoting members 105a, 107a, 109a, and 111a may be independently adjustable with respect to arms 105, 107, 109, and 111, respectively. In some embodiments, translation of actuators 105b, 107b, 109b, and 111b may cause a corresponding element, such as an internal pin, set screw or the like, to urge pivoting members 105a, 107a, 109a, and 111a to pivot outwards on a corresponding pin within a corresponding socket thereby enabling travel of pivoting members 105a, 107a, 109a, and 111a inwards and outwards with respect to arms 105, 107, 109, and 111, respectively. In some embodiments, pivoting members 105a, 107a, 109a, and 111a may pivot outwards, for example, within a range of 0-25 degrees, and more particularly within a range of 0-15 degrees with respect to arms 105, 107, 109, and 111.

Figure 7:
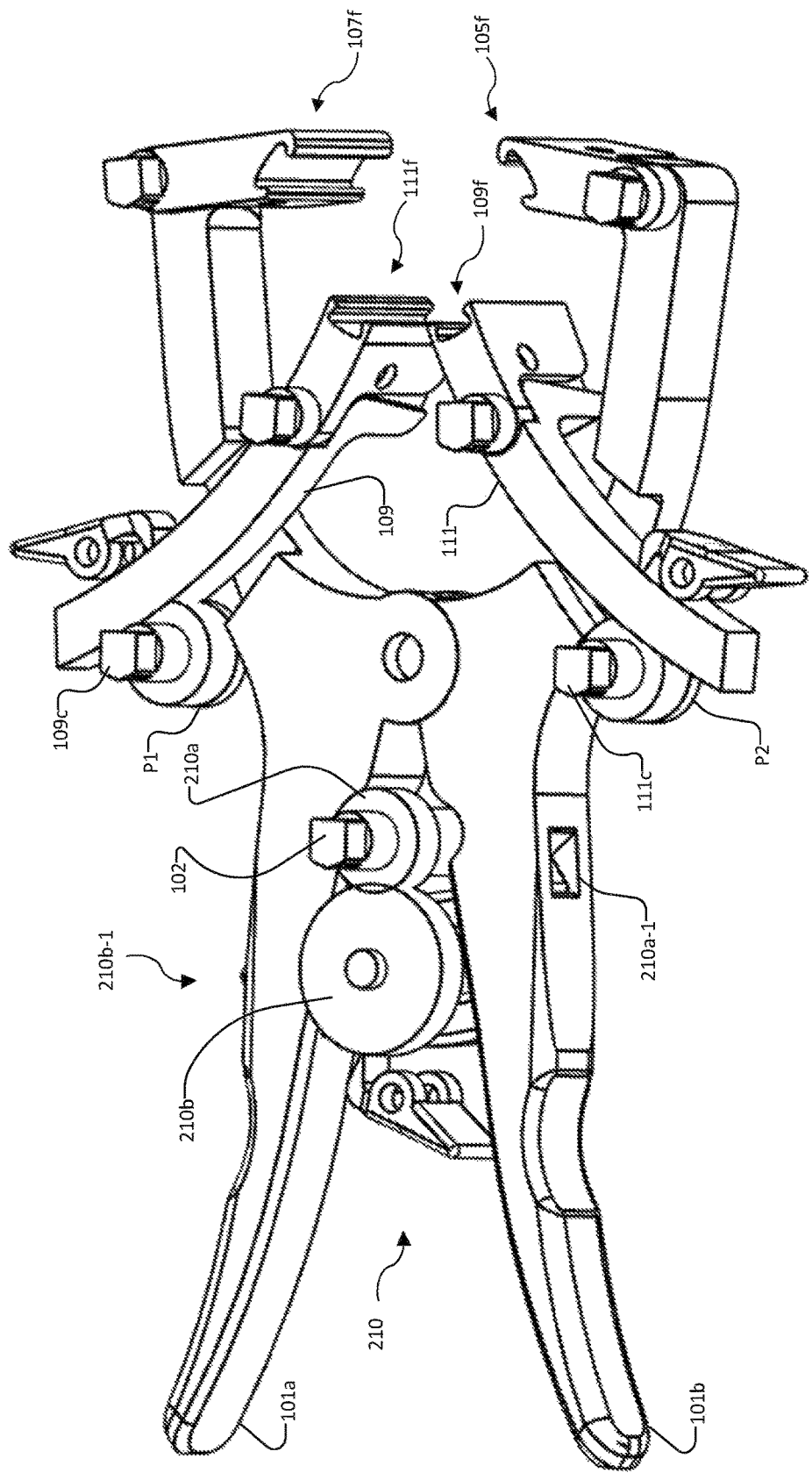
FIG. 7 is a cutaway view of the retractor system of FIG. 1 in accordance with the principles of the disclosure.

Pivoting members 105a, 107a, 109a, and 111a may include corresponding blade attachment mechanisms 105f, 107f, 109f, and 111f, respectively (see FIG. 7). The blade attachment mechanisms 105f, 107f, 109f, and 111f, may each include a dovetail groove having a geometry that facilitates secure engagement with a corresponding one of blades 205, 207, 209, and 211. For example, blade attachment mechanisms 105f, 107f, 109f, and 111f, may have an indent portion on an inside surface thereof facilitating secure engagement with an outdent portion disposed on an outside surface of blades 205, 207, 209, and 211 respectively. In some embodiments, the dovetail grooves of the blade attachment mechanisms 105f, 107f, 109f, and 111f, are tapered, and may for example be conically tapered, from one end to the other end to further securely retain blades 205, 207, 209, and 211. In other embodiments, the blade attachment mechanisms 105f, 107f, 109f, and 111f, may take alternate shapes, and have varying configurations provided that the shape thereof can securely engage with a corresponding one of blades 205, 207, 209, and 211. For example, an indent such as a square channel, hexagonal channel, or the like dimensioned to match to a corresponding outdent. Additionally, the blade attachment mechanisms 105f, 107f, 109f, 111f may have an outdent portion (rather than an indent portion as illustrated) and blades 205, 207, 209, and 211 may have an indent portion (rather than an outdent portion as illustrated).

Figure 9:
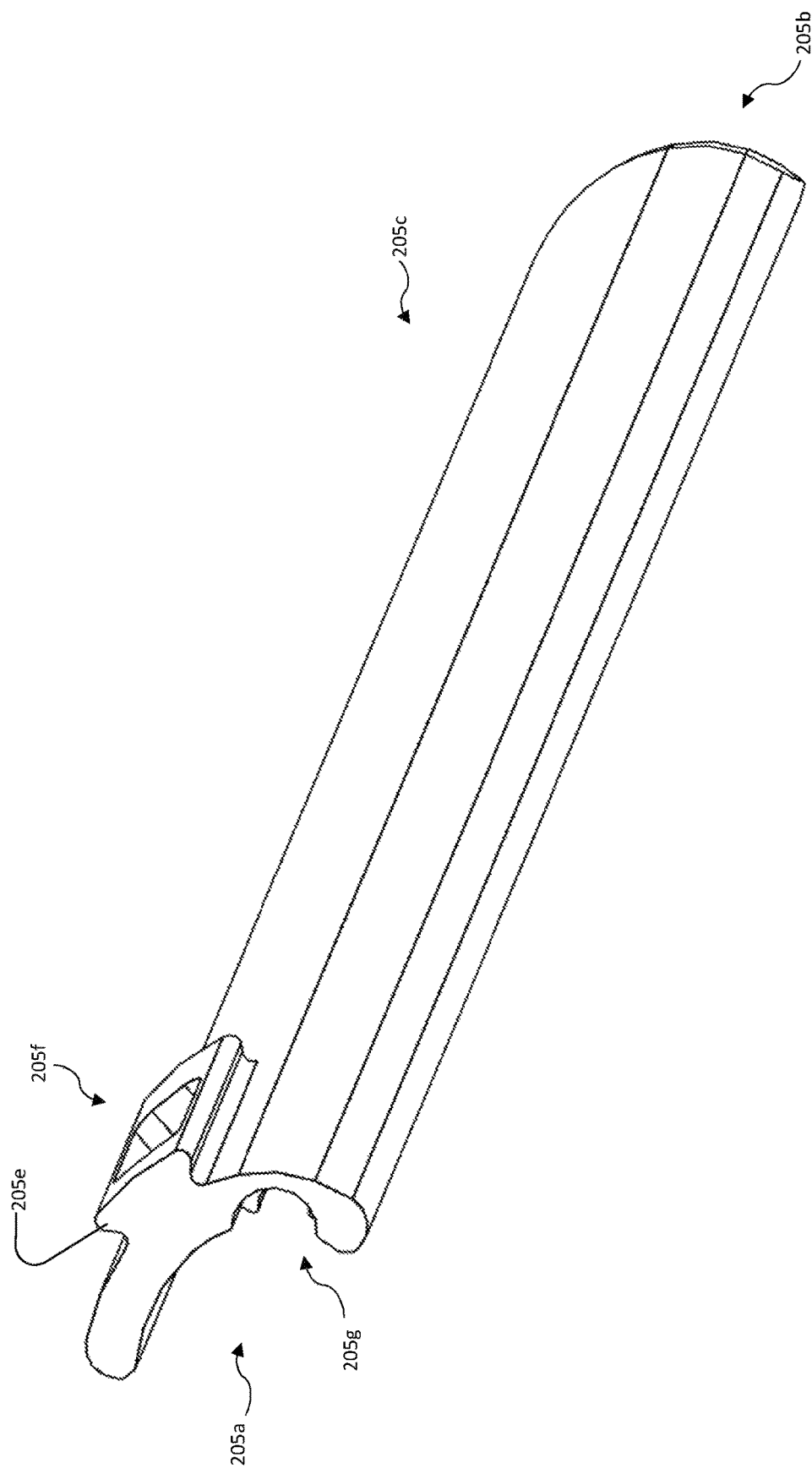
FIG. 9 is a perspective view of an exemplary blade for use with the retractor system of FIG. 1 in accordance with the principles of the disclosure.
Figure 10:
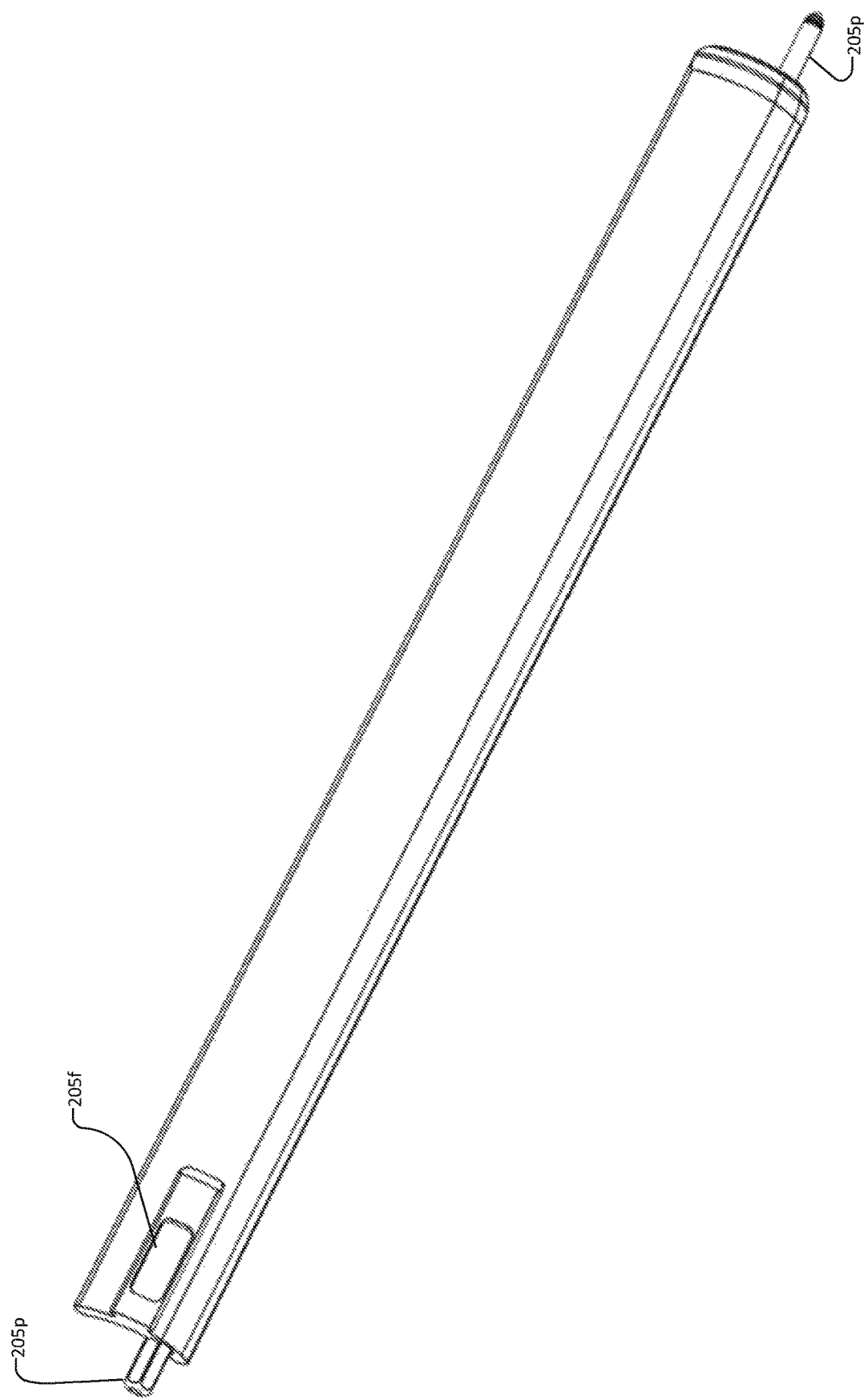
FIG. 10 is an alternate perspective view of an exemplary blade and pin for use with the retractor system of FIG. 1 in accordance with the principles of the disclosure.
Figure 11:
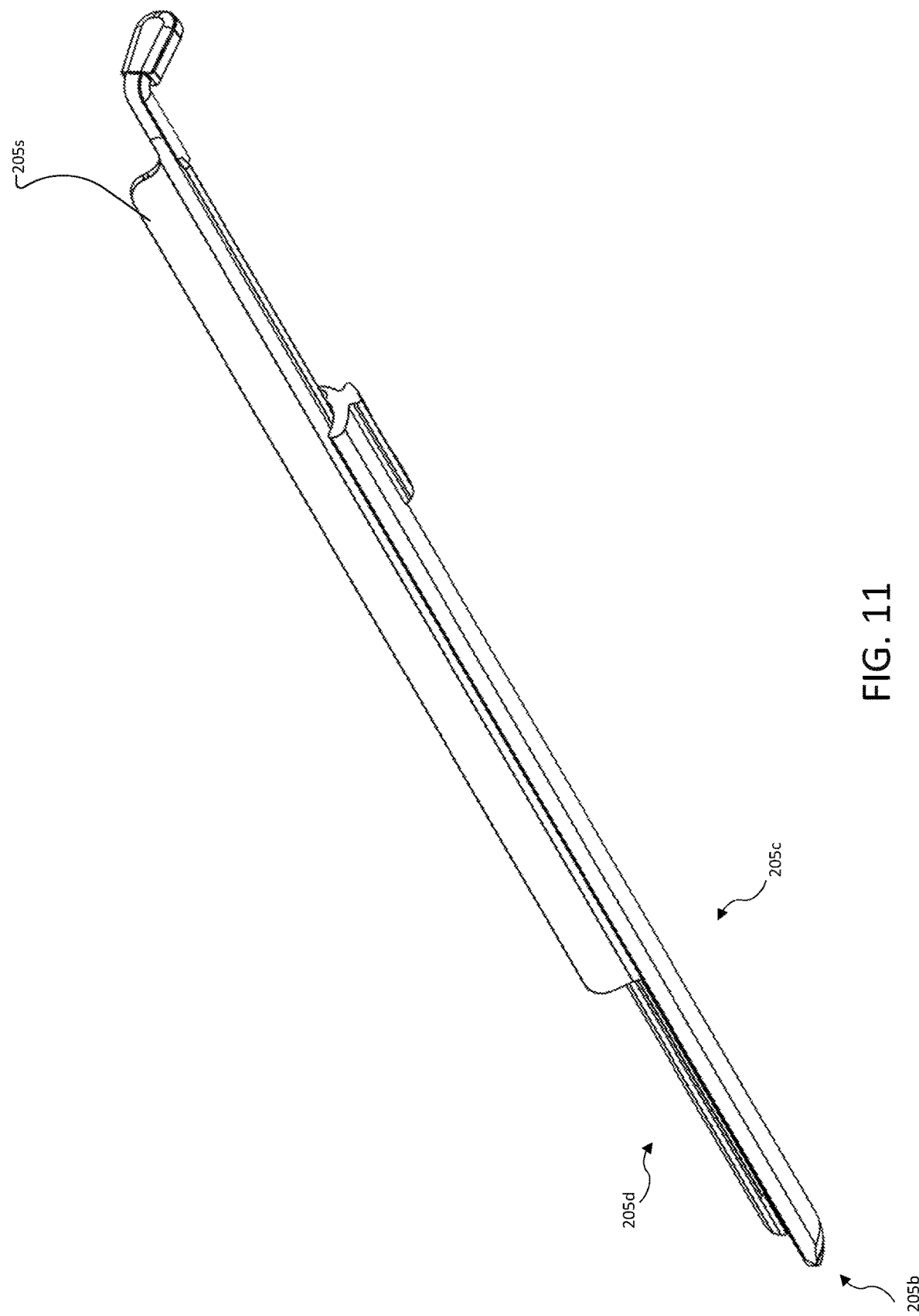
FIG. 11 is a perspective view of an exemplary blade and shim for use with the retractor system of FIG. 1 in accordance with the principles of the disclosure.

Referring generally to FIGS. 9-13B exemplary blades, shims, and dilators for use with, e.g., retractor system 100, are disclosed. Referring to FIGS. 9-11, an exemplary blade, e.g., first blade 205 is illustrated. It shall be understood that characteristics of first blade 205 may be found throughout each of blades 205, 207, 209, and 211 and the foregoing description is described with respect to first blade 205 solely for convenience of explanation. Moreover, although first blade 205 is illustrated as a relatively long and narrow curved blade 205 it can take any shape suitable for any particular type of surgery application. Indeed, it is contemplated that retractor system 100 is suitable for a multitude of different blades having different lengths, widths, and cross sectional shapes thereof that can couple and uncouple to secondary blades, tools, and shims. For example, relatively shorter and wider blades having generally planar surfaces are contemplated. Furthermore, blade 205 may feature any number or type of secondary coupling members where shims, for example, may couple thereto. In at least one embodiment, blade 205 may have a relatively narrow portion at one end and fan out to a relatively wider portion at the opposite end, i.e., the blade 205 may have a width that increases along the length thereof from one end to the other end. Additionally, blade 205 may include channels, grooves, indents, outdents, etc. for fixation of secondary members such as shims, light fixtures other diagnostic tools such as endoscopes, electrodes, temperature sensors, suction devices, and etc.

In the exemplary embodiment, blade 205 has a proximate side 205 a, a distal side 205b opposite the proximate side, an outside surface 205c and an inside surface 205d opposite the outside surface 205c. The proximate side 205a may be operably coupled to a distal end of pivoting member 105a via an engagement feature 205e disposed on the outside surface 205c of blade 205, for example. In some embodiments, blade 205 may include an elastic material allowing it to deflect at least partially. Additionally, in some embodiments a blade removal instrument may be required to install and/or remove blade 205 from a blade attachment mechanism.

In the disclosed embodiment, engagement feature 205e is the outdent portion of a dovetail groove, i.e., the dovetail. In other embodiments, engagement feature 205e may be a lap joint, tongue and groove type joint, a doweled butt joint, etc. In the exemplary embodiment, engagement feature 205e features an indent portion 205f. Indent portion 205f may be a socketed portion facilitating secured engagement and retention with blade attachment mechanism 105f. For example, indent portion 205f may house a spring clip (not illustrated) to hold blade 205 in secure engagement with blade attachment mechanism 105f. In embodiments that include a spring clip, a corresponding release tool or lever may be inserted into the indent portion 205f to release the biasing force of the spring and thereby uncouple the blade 205 from blade attachment mechanism 105f. In other embodiments, engagement feature 205e may have an aperture for running a diagnostic tool such as an electrode or endoscope there through. In some embodiments, blade 205 may be conductive such that it may communicate with an external diagnostic tool (not illustrated). For example, blades may include a conductive material such as a metal like copper and be conductive and/or have terminals for electrical conduction between conductive pads placed external to retractor system 100. In some embodiments, blade 205 may include partially conductive features, e.g., a semiconductor and/or other passive electrical devices such as resisters, diodes, and etc. In other embodiments, blade 205 may be an insulator such that it does not interfere with electrical signal processing of the aforementioned electrical devices.

In the exemplary embodiment, first blade 205 may include a longitudinal groove 205g extending longitudinally along the inside surface 205d that is sized accordingly to house and retain a corresponding pin 205p therein. In at least one embodiment, pin 205p may securely attach to a vertebrae of a patients spine by socketing in to the vertebrae or screwing into the vertebrae. In some embodiments, pin 205p may be a conductive pin having a sensor at a distal end thereof or pin 205p may be a hollow pin that houses electrical components and wiring therein. In other embodiments pin 205p is purely mechanical in nature. In at least one embodiment, pin 205p may be used to facilitate attachment of a shim 205s to an inside surface 205d of blade 205. Shim 205s may laterally extend from a side surface of the blade 205 and include a gripping portion at a proximate side thereof. Shim 205s may also extend from the blade 205 to increase the operative length thereof and/or extend laterally to increase the operative width thereof. In some embodiments, the first, second, third, and fourth blades 105, 107, 109, 111 are each configured to operably couple to a corresponding first, second, third, and fourth shim laterally projecting from a side portion thereof. In other embodiments, diagnostic tools such as an electrode, endoscope, fiber optic, light emitting diode or the like may extend along groove 205g. In other embodiments still, a second groove (not illustrated) similar to groove 205g may be provided so that a combination of the above described features may be used. For example, groove 205g may house a corresponding pin 205p and the second groove (not illustrated) may enable a diagnostic tool or the like to extend along the second groove (not illustrated).

Figure 12:
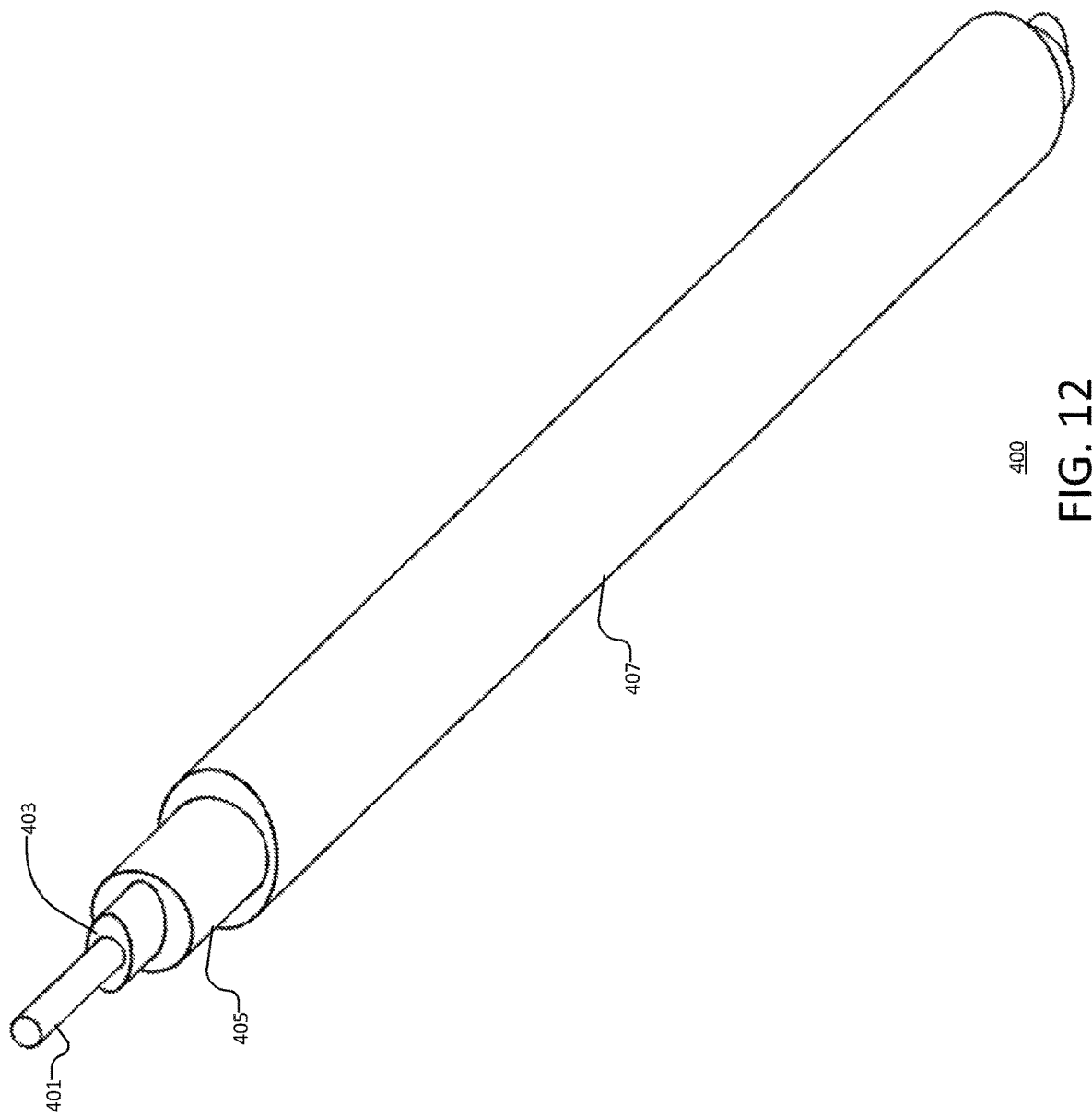
FIG. 12 is a perspective view of an exemplary set of nested dilators for coordinated use with the retractor system of FIG. 1 in accordance with the principles of the disclosure.

Referring to FIG. 12 an exemplary set of nested dilators 400 is illustrated. Exemplary dilators 400 may include a neuro monitoring sensor or the like to help guide insertion of the dilators through muscle fibers. The set of nested dilators 400 may include a series of dilators having alternating circular and ellipsis (oval) cross sectional shapes or oblong cross sectional shapes. For example, a first dilator 401 having a relatively small circular cross section is surrounded by a second dilator 403 having an ellipsis, or oval shaped cross section. The size and shape of the circular cross section of the first dilator 401 may be defined by a radius extending from a center point thereof and the shape of the ellipsis cross section may be defined by a major axis and a minor axis extending perpendicularly with respect to one another from a center point thereof.

In the exemplary embodiment, the second dilator 403 may, for example, have an ellipsis or elliptical cross section, or other cross sections, for example bi-convex or elongated and substantially flat sides with convex ends, and may have a curvature but may not be circular or elliptical, some such embodiments having a minor axis roughly corresponding to the radius of the circular cross section of first dilator 401. For example, the minor axis of the ellipsis cross section of the second dilator 403 may only be slightly larger than the radius of the circular cross section of the first dilator 401, and the major axis of the ellipsis cross section of the second dilator 403 may be relatively larger than the radius of the circular cross section of the first dilator 401 and the minor axis of the ellipsis cross section of the second dilator 403. In some embodiments, the major axis of the ellipsis cross section of second dilator 403 may be roughly twice as large as the radius of the circular cross section of first dilator 401. In some embodiments, the major axis of the ellipsis cross section of the second dilator 403 may be twice as large as the minor axis of the ellipsis cross section of the second dilator 403. At least one advantage to this arrangement of alternating cross sections is that the second dilator 403 may be insert around the first dilator 401 between fibers of a muscle, e.g., the paraspinous muscle, such that the major axis of the second dilator 403 is initially arranged parallel with the fibers of the paraspinous muscle and can therefore be insert around the first dilator 401. Once inserted around the first dilator 401, second dilator 403 can be rotated such that the major axis of second dilator 403 is perpendicular to the orientation of the fibers of the paraspinous muscle thereby gently separating the fibers by orienting the second dilator 403 such that the major axis area of the second dilator 403 gently and controllably applies pressure to separate the fibers.

A third dilator 405 having a circular cross section may be insert around the second dilator 403. The size and shape of the circular cross section of the third dilator 405 may be defined by a radius extending from a center point thereof. For example, the third dilator 405 may have a circular cross sectional shape having a radius roughly corresponding to the major axis of the second dilator 403. The third dilator 405 can freely rotate around the second dilator 403 and features a circular cross section having a radius that is only slightly larger than the cross sectional major axis of the second dilator 403. A fourth dilator 407 having an ellipsis cross section (oval) may be insert around the third dilator 405. The fourth dilator 407 may be defined by an ellipsis cross section having a minor axis that is only marginally larger than the cross sectional radius of the third dilator 405, i.e., the cross sectional minor axis of the fourth dilator roughly corresponds to the cross sectional radius of the third dilator 405. Additionally, the cross sectional major axis of the fourth dilator 407 is relatively larger than the cross sectional radius of the third dilator 405 and the cross sectional minor axis of the fourth dilator. In some embodiments, the major axis of the ellipsis cross section of fourth dilator 407 may be roughly twice as large as the radius of the circular cross section of third dilator 405. In some embodiments, the major axis of the ellipsis cross section of the fourth dilator 407 may be twice as large as the minor axis of the ellipsis cross section of the fourth dilator 407. At least one advantage to this arrangement of alternating cross sections is that the fourth dilator 407 may be insert around the third dilator 405 between fibers of a muscle, e.g., the paraspinous muscle, such that the major axis of the fourth dilator 407 is initially arranged parallel with the fibers of the paraspinous muscle and can therefore be insert around the third dilator 405. Once inserted around the third dilator 405, fourth dilator 407 can be rotated such that the major axis of fourth dilator 407 is perpendicular to the orientation of the fibers of the paraspinous muscle thereby gently separating the fibers by orienting the fourth dilator 407 such that the major axis area of the fourth dilator 407 gently and controllably applies pressure to separate the fibers.

Figure 13A:
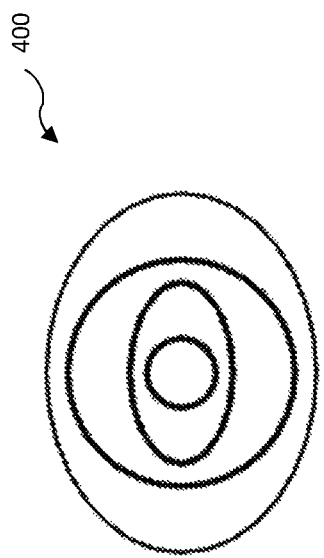
FIG. 13A is a top down view of the set of nested dilators of FIG. 12.
Figure 13B:
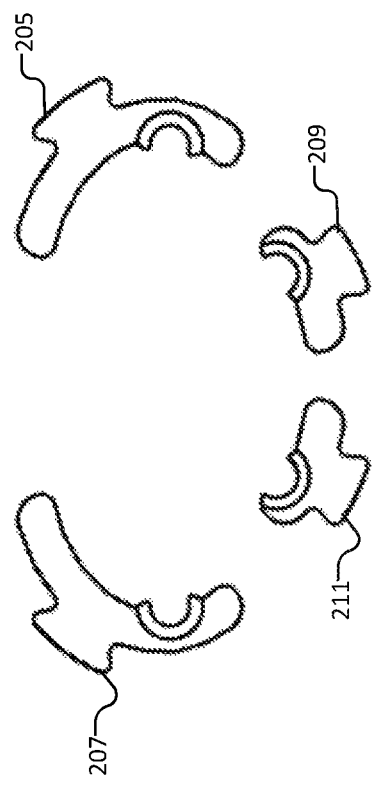
FIG. 13B is a top down view of a plurality of blades for use with the retractor system of FIG. 1 in accordance with the principles of the disclosure.

FIG. 13A is a top down view of the set of nested dilators 400 as explained above. As illustrated a set of nested dilators 400 that may sequentially gently separate fibers of a muscle are illustrated. The set of nested dilators 400 may be insert sequentially and rotated on an as needed basis to gently dilate an anatomical feature. FIG. 13B is a top down view of blades 205, 207, 209, and 211. As illustrated blades 205, 207 are relatively larger in width than blades 209, and 211.

Figure 14:
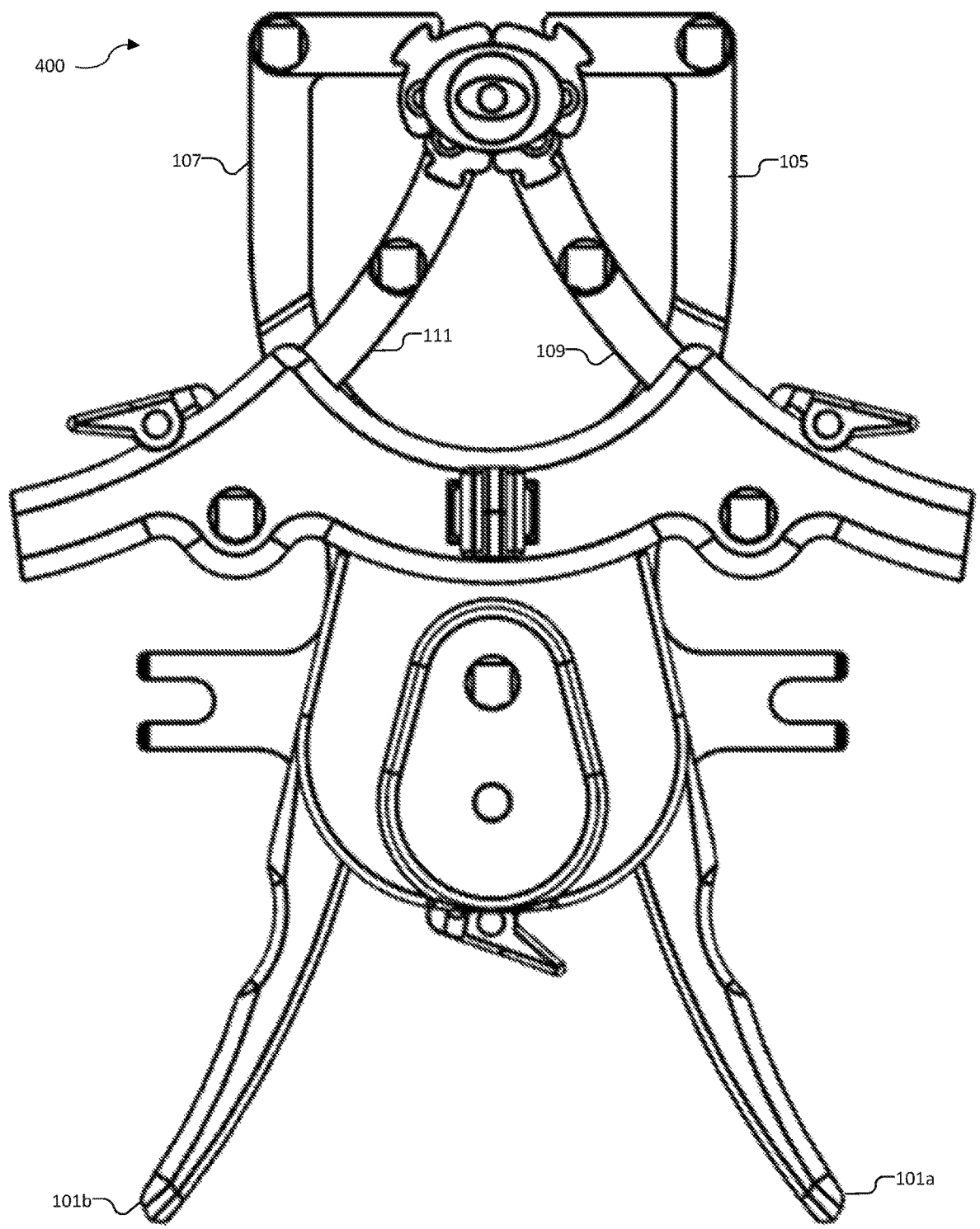
FIG. 14 is a top down view of an exemplary retractor system having a plurality of blades surrounding a set of nested dilators in accordance with the principles of the disclosure.
Figure 15:
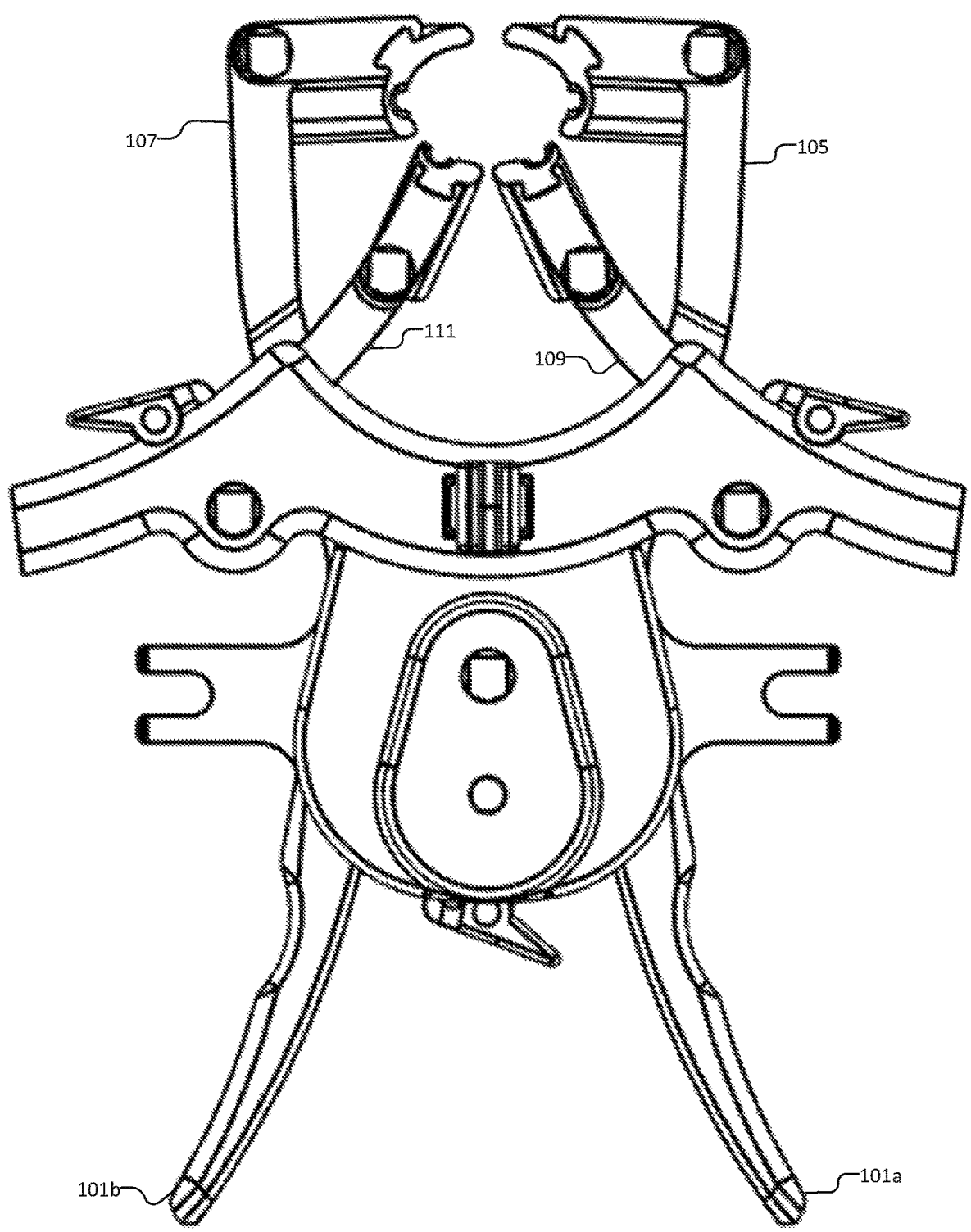
FIG. 15 is a top down view of an exemplary retractor system of FIG. 14 in a first partially expanded position after removal of the set of nested dilators in accordance with the principles of the disclosure.
Figure 16:
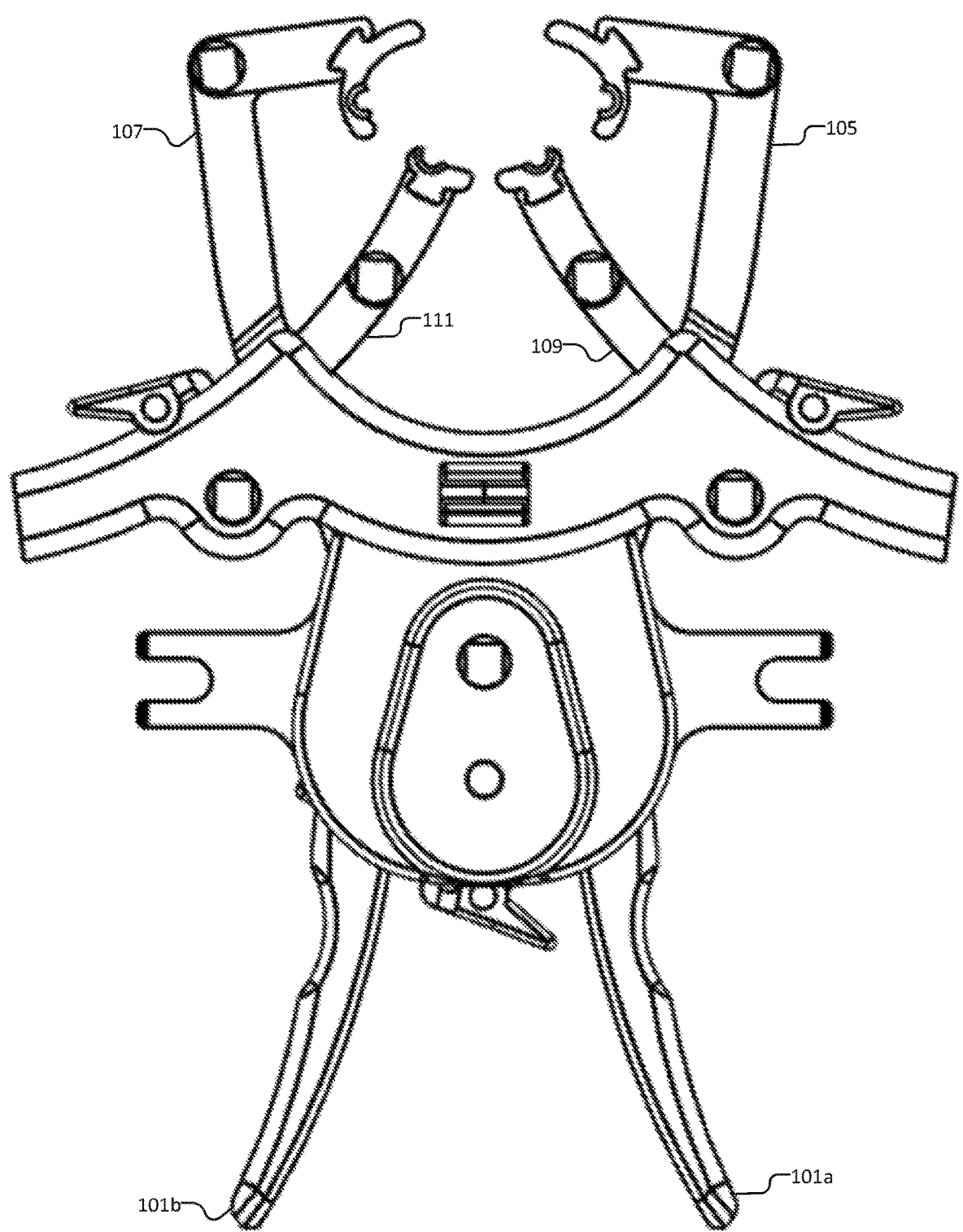
FIG. 16 is a top down view of an exemplary retractor system of FIG. 14 in the first partially expanded position in accordance with the principles of the disclosure.
Figure 17:
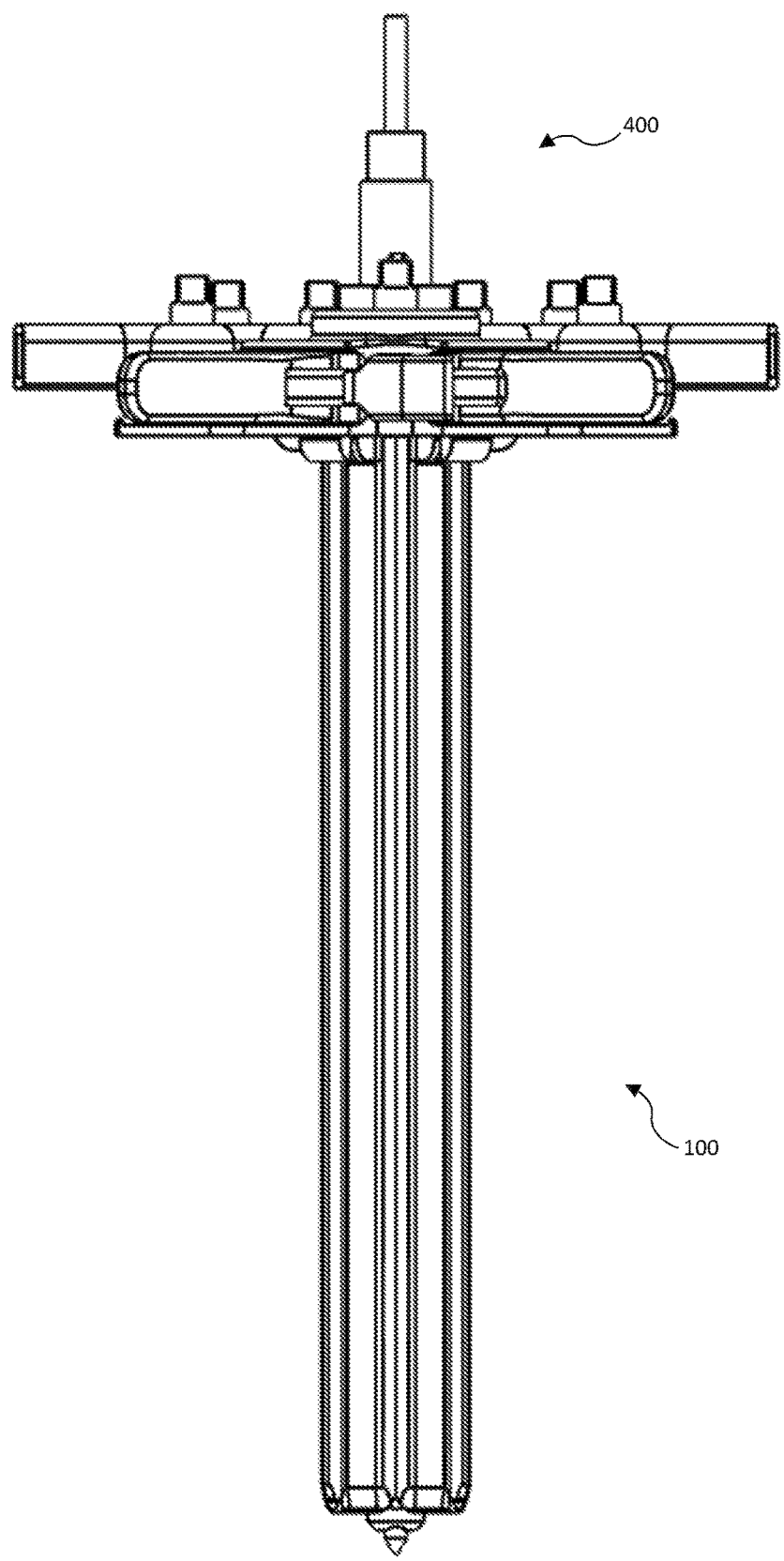
FIG. 17 is a side view of the exemplary retractor system of FIG. 14 having a plurality of blades surrounding a set of nested dilators in accordance with the principles of the disclosure.

FIGS. 14-19 illustrate various positions and modes of operation of retractor system 100 in use with the set of nested dilators 400. For example, in FIG. 14, retractor system 100 is shown in a closed position where arms 105, 107 are closed and surround, at least partially, the set of nested dilators 400. Additionally, arms 109, 111 are fully extended and surround, at least partially, the set of nested dilators 400. In FIG. 14, the inside surfaces of blades 205, 207, 209, and 211 (not labelled in FIG. 14) together surround and contact an outside surface of a fourth dilator 407 (not labelled in FIG. 14). For example, the blades 205, 207, 209, and 211 surround and contact a set of nested dilators 400. For example still, a side surface of each of blades 205, 207, 209, and 211 contacts an adjoining side surface of a different adjacent blade of the blades 205, 207, 209, and 211 thereby forming a closed shape. FIG. 17 is a side view of the arrangement of FIG. 14.

Figure 18:
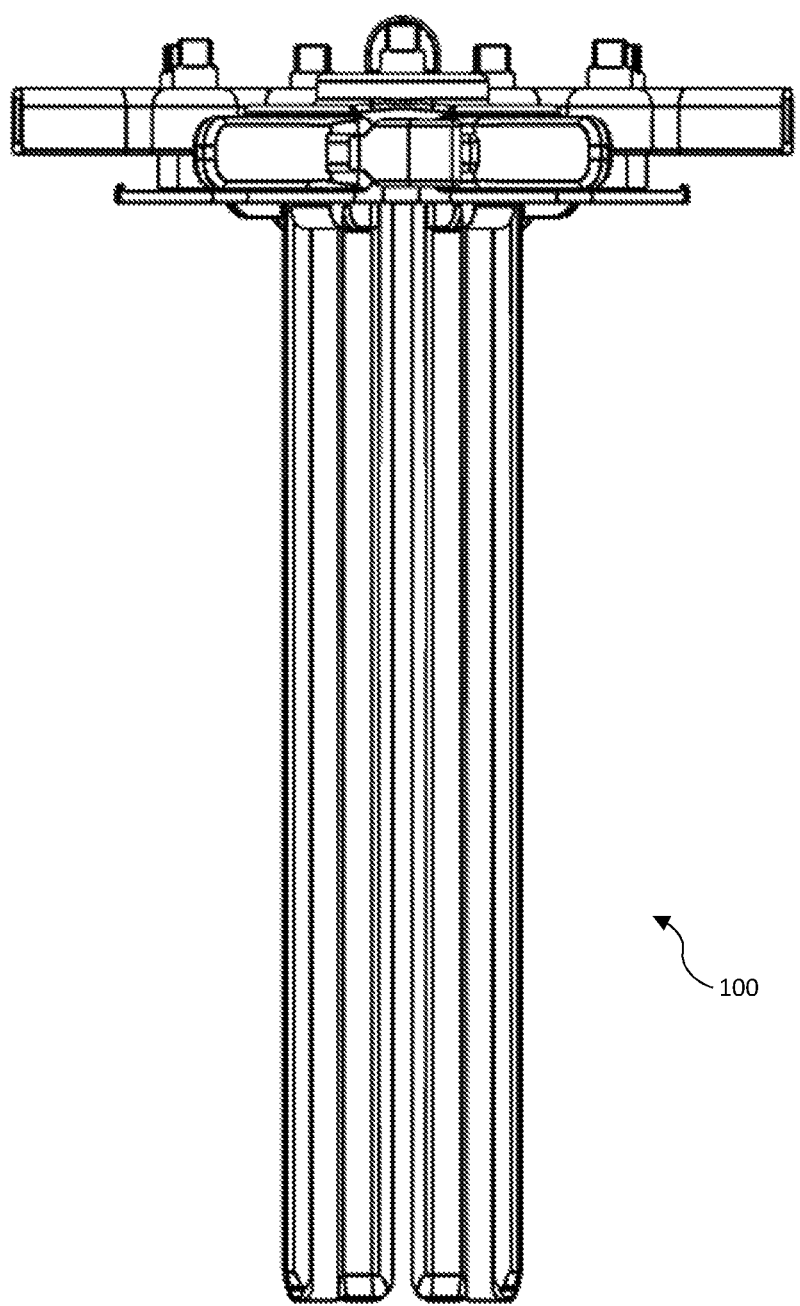
FIG. 18 is a side view of the exemplary retractor system of FIG. 14 in a second expanded position in accordance with the principles of the disclosure.
Figure 19:
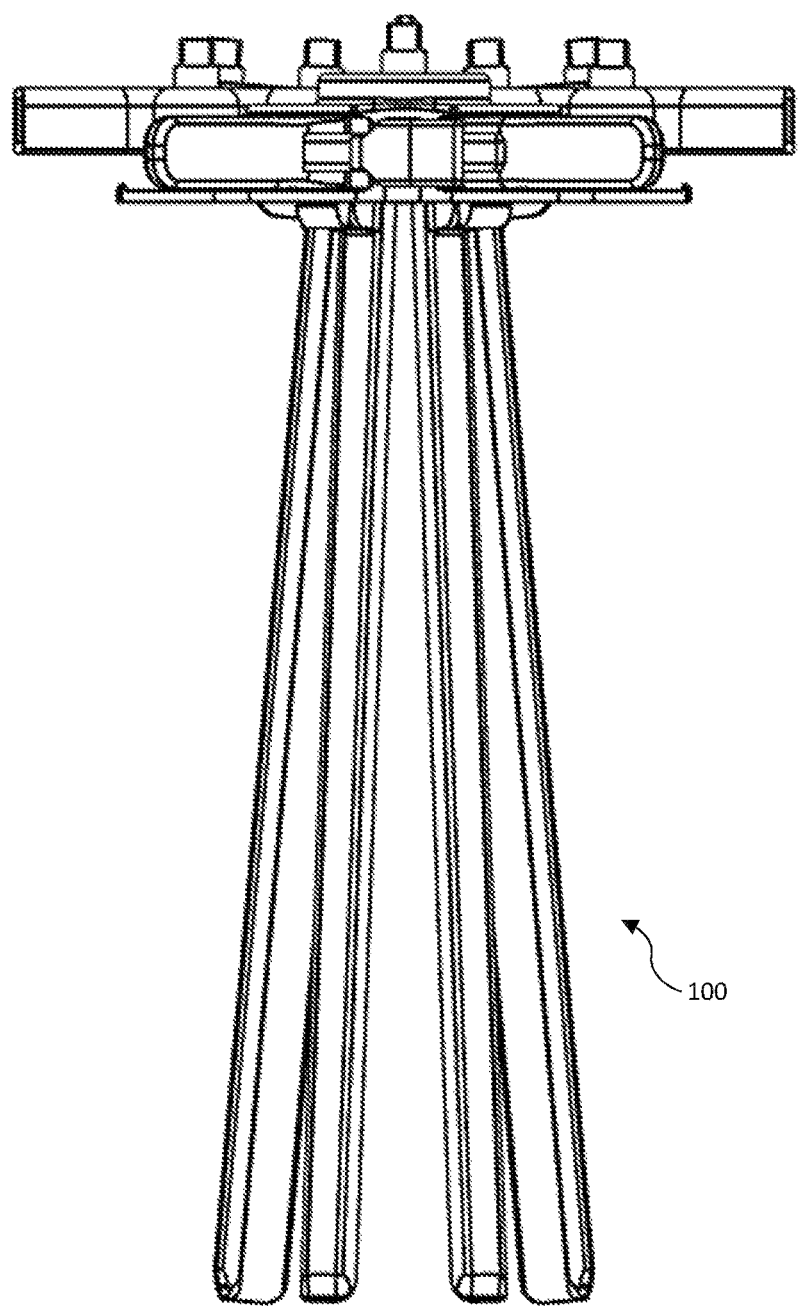
FIG. 19 is a side view of the exemplary retractor system of FIG. 14 in the second expanded position in accordance with the principles of the disclosure.

In FIG. 15, the set of nested dilators 400 is removed and the retractor system 100 is adjusted to a first partially opened position where arms 105, 107 are partially opened and arms 109, 111 are partially contracted. FIG. 18 is a side view of the first partially opened arrangement of FIG. 15. In FIG. 16, the retractor system is adjusted to a second partially opened position where arms 105, 107 are further opened and arms 109, 111 are further contracted. FIG. 18 is a side view of the second partially opened arrangement of FIG. 16. FIG. 19 shows the angulation of each blade being adjusted outward approximately 15 degrees from the side view of FIG. 18.

What is claimed is:

1. A retractor system for enabling access to a surgical site, comprising:
   a primary retractor assembly configured to open and close a first arm and a second arm along a first path of travel, the primary retractor assembly including:
   a handle assembly having first and second handles operably coupled to the first and second arms and configured to open and close the first and second arms, respectively, the first and second arms operably coupled to first and second pivoting members at a distal end thereof, respectively, the first and second pivoting members being configured to operably couple to first and second blades, respectively;
   a first actuator and a second actuator configured to actuate the first and second pivoting members, respectively, the first and second pivoting members configured to independently angulate the first and second blades, respectively;
   a primary actuator configured to actuate a primary pinion gear mechanism operably coupled to the first and second handles and configured to open and close the first and second blades along the first path upon actuation of the primary actuator; and a secondary retractor assembly configured to couple and uncouple with the primary retractor assembly and independently extend and contract a third arm, the secondary retractor assembly including:
a first channel for operably retaining the third arm therein, the first channel defining a second path of travel, the third arm being configured to travel along the second path;
a third actuator disposed adjacent the first channel and operably configured to extend and contract the third arm via a first pinion gear mechanism;
the third arm being operably coupled to a third pivoting member at a distal end thereof, the third pivoting member being configured to operably couple and uncouple with a third blade; and
a fifth actuator configured to actuate the third pivoting member, the third pivoting member being configured to independently angulate the third blade, upon actuation of the fifth actuator.

2. The retractor system of claim 1, wherein the secondary retractor assembly is further configured to couple and uncouple from the primary retractor assembly via a first recessed key portion and a second recessed key portion disposed on the first and second arms, respectively, and a turnkey projecting from a central portion of the primary retractor assembly through a central aperture of the secondary retractor assembly.

3. The retractor system of claim 1, wherein the primary retractor assembly is further configured to independently open and close the first arm along the first path upon movement of the first handle and independently open and close the second arm along the first path upon movement of the second handle.

4. The retractor system of claim 1, wherein the primary pinion gear mechanism is operably coupled to the first and second handles and configured to provide a controlled mechanical advantage to open and close the first and second arms along the first path upon actuation of the primary actuator.

5. The retractor system of claim 1, wherein the secondary retractor assembly is further configured to extend and withdraw a fourth arm, the secondary retractor assembly further comprising:
a second channel for operably retaining the fourth arm therein, the second channel defining a third path of travel, the fourth arm being configured to travel along the third path;
a fourth actuator disposed adjacent the second channel and operably configured to extend and contract the fourth arm via a second pinion gear mechanism;
the fourth arm being operably coupled to a fourth pivoting member at a distal end thereof, and being configured to operably couple and uncouple with a fourth blade; and
a sixth actuator configured to actuate the fourth pivoting member the fourth pivoting member being configured to independently angulate the fourth blade upon actuation of the sixth actuator.

6. The retractor system of claim 5, wherein the first and second pivoting members each further comprise a corresponding pin and socket mechanism and a corresponding blade attachment mechanism having a dovetail groove configured to engage a corresponding one of the first blade and second blade, respectively, and
wherein the third and fourth pivoting members each further comprise a corresponding pin and socket mechanism and a corresponding blade attachment mechanism having a dovetail groove configured to engage a corresponding one of the third blade and fourth blade, respectively.

7. The retractor system of claim 5, wherein the primary retractor assembly further comprises a primary retention lever configured to control opening and closing of the first and second arms.

8. The retractor system of claim 7, wherein the primary retention lever engages a rack portion fixedly coupled to the second arm to thereby control opening and closing of the first and second arms.

9. The retractor system of claim 7, wherein the secondary retractor assembly further comprises a first retention lever configured to engage the third arm to control extension and contraction of the third arm and a second retention lever configured to engage the fourth arm to control extension and contraction of the fourth arm.

10. The retractor system of claim 5, wherein the first, second, third, and fourth blades are each configured to operably couple to a corresponding first, second, third, and fourth shim.

11. The retractor system of claim 5, wherein at least one of the first, second, third, and fourth blades is configured to surround at least a portion of the at least one dilator and contact an outside surface of the at least one dilator.

12. The retractor system of claim 5, wherein at least one of the first, second, third, and fourth blades is configured to surround at least a portion of a set of nested dilators and contact an outside surface of an outermost dilator of the set of nested dilators.

13. The retractor system of claim 5, wherein at least one of the first, second, third, and fourth blades is configured to surround and contact at least a portion of an outermost dilator of a set of nested dilators comprising:
a first dilator having a circular cross section;
a second dilator having an ellipsis shaped cross section and surrounding the first dilator; and
a third dilator having a circular cross section and surrounding the second dilator;
a fourth dilator having an ellipsis shaped cross section and surrounding the third dilator,
wherein the first dilator is an innermost dilator and the fourth dilator is an outermost dilator.

14. The retractor system of claim 5, wherein the first channel has an arcuate shape and the third arm has a corresponding arcuate shape, the arcuate shape of the first channel defining the second path,
wherein the second channel has an arcuate shape and the fourth arm has a corresponding arcuate shape, the arcuate shape of the second channel defining the third path, and
wherein a radius of curvature of the first path is greater than a radius of curvature of the second path and a radius of curvature of the third path.

15. The retractor system of claim 1, wherein the primary retractor assembly further comprises at least one table mounting portion configured to mount to a table thereby fixedly coupling the retractor system stably to the table.

16. A method for enabling access to a surgical site, comprising:
providing a primary retractor assembly configured to open and close a first arm and a second arm along a first path of travel, the primary retractor assembly including:
a handle assembly having first and second handles operably coupled to the first and second arms and configured to open and close the first and second arms, respectively, the first and second arms operably coupled to first and second pivoting members at a distal end thereof, respectively, the first and second pivoting members being configured to operably couple to first and second blades, respectively;
a first actuator and a second actuator configured to actuate the first and second pivoting members, respectively, the first and second pivoting members configured to independently angulate the first and second blades, respectively;
a primary actuator configured to actuate a primary pinion gear mechanism operably coupled to the first and second handles and configured to open and close the first and second blades along the first path upon actuation of the primary actuator;
providing a secondary retractor assembly configured to couple and uncouple with the primary retractor assembly and independently extend and contract a third arm, the secondary retractor assembly including:
a first channel for operably retaining the third arm therein, the first channel defining a second path of travel, the third arm being configured to travel along the second path;
a third actuator disposed adjacent the first channel and operably configured to extend and contract the third arm via a first pinion gear mechanism:
the third arm being operably coupled to a third pivoting member at a distal end thereof, the third pivoting member being configured to operably couple and uncouple with a third blade; and
a fifth actuator configured to actuate the third pivoting member, the third pivoting member being configured to independently angulate the third blade, upon actuation of the fifth actuator;
opening at least one of the first arm and the second arm along the first path; and
closing at least one of the first arm and the second arm along the first path.

17. The method for enabling access to a surgical site of claim 16, comprising:
extending, independently, the third arm along the second path; and
contracting, independently, the third arm along the second path.

18. The method for enabling access to a surgical site of claim 17, comprising:
independently angulating at least one blade chosen from the first blade, the second blade, and the third blade.

19. The method for enabling access to a surgical site of claim 18, comprising:
providing a set of nested dilators including:
a first dilator having a circular cross section;
a second dilator having an ellipsis shaped cross section and surrounding the first dilator; and
a third dilator having a circular cross section and surrounding the second dilator;
a fourth dilator having an ellipsis shaped cross section and surrounding the third dilator,
wherein the first dilator is an innermost dilator and the fourth dilator is an outermost dilator; and
dilating a paraspinous muscle before the steps of: opening/closing at least one of the first arm and the second arm along the first path.

20. A retractor system for enabling access to a surgical site, comprising:
a primary retractor assembly configured to open and close a first arm and a second arm along a first path of travel, the primary retractor assembly including:
a handle assembly having first and second handles operably coupled to the first and second arms and configured to open and close the first and second arms independently upon opening and closing of the first and second handles, the first and second arms operably coupled to first and second pivoting members at a distal end thereof, respectively, the first and second pivoting members being configured to operably couple to first and second blades, respectively,
a first actuator and a second actuator configured to actuate the first and second pivoting members, respectively, the first and second pivoting members configured to independently angulate the first and second blades upon actuation of the first and second actuators, respectively, the first and second pivoting members each comprising a corresponding pin and socket mechanism and a corresponding blade attachment mechanism, the corresponding blade attachment mechanism comprising a dovetail groove configured to engage a corresponding one of the first blade and second blade, respectively;
a primary actuator configured to actuate a primary pinion gear mechanism comprising a primary gear, a secondary gear, and a tertiary gear, the primary pinion gear mechanism being operably coupled to the first and second handles and configured to provide a controlled mechanical advantage to simultaneously open and close the first and second arms along the first path upon actuation of the primary actuator; and
a primary retention lever configured to control opening and closing of the first and second arms; and
a secondary retractor assembly, configured to couple and uncouple with the primary retractor assembly and independently extend and contract a third arm and a fourth arm, respectively, the secondary retractor assembly including:
a first arcuate channel for operably retaining the third arm therein and a second arcuate channel for operably retaining the fourth arm therein, the first arcuate channel defining a second arcuate path of travel and the second arcuate channel defining a third arcuate path of travel, the third arm being configured to travel along the second path and the fourth arm being configured to travel along the third path;
a third actuator disposed adjacent the first channel and operably configured to extend and contract the third arm via a first pinion gear mechanism and a fourth actuator disposed adjacent the second channel and operably configured to extend and contract the fourth arm via a second pinion gear mechanism;
the third and fourth arms being operably coupled to third and fourth pivoting members at a distal end thereof, respectively, the third and fourth pivoting members being configured to operably couple and uncouple with third and fourth blades, respectively;
fifth and sixth actuators configured to actuate the third and fourth pivoting members, respectively, the third and fourth pivoting members configured to independently angulate the third and fourth blades, respectively, upon actuation of the fifth and sixth actuators, respectively, the third and fourth pivoting members each comprising corresponding a pin and socket mechanism and a corresponding blade attachment mechanism, each corresponding blade attachment mechanism comprising a dovetail groove configured to engage a corresponding one of the third blade and fourth blade, respectively; and a first retention lever configured to engage the third arm to control extension and contraction of the third arm and a second retention lever configured to engage the fourth arm to control extension and contraction of the fourth arm.

* * * * *